United States Patent

Atherton et al.

[11] 4,250,085
[45] Feb. 10, 1981

[54] ACYL DERIVATIVES

[75] Inventors: Frank R. Atherton, Welwyn Garden City; Michael J. Hall, Welwyn; Cedric H. Hassall, Welwyn; Robert W. Lambert, Welwyn; Peter S. Ringrose, Harston, all of England

[73] Assignee: Hoffmann-La Roche Inc., Nutley, N.J.

[21] Appl. No.: 971,156

[22] Filed: Dec. 20, 1978

[30] Foreign Application Priority Data

Dec. 23, 1977 [GB] United Kingdom ............... 53668/77
Nov. 20, 1978 [GB] United Kingdom ............... 45272/78

[51] Int. Cl.³ ..................... C07C 103/52; C07G 7/00; A61K 37/00
[52] U.S. Cl. .............. 260/112.5 R; 424/177
[58] Field of Search ................. 260/112.5 R; 424/177

[56] References Cited
U.S. PATENT DOCUMENTS
4,016,148  4/1977  Atherton et al. ............. 260/112.5 R OTHER PUBLICATIONS
Huber, J. Med. Chem., 18, 103 (1975).

Primary Examiner—Delbert R. Phillips
Assistant Examiner—Blondel Hazel
Attorney, Agent, or Firm—Jon S. Saxe; Bernard S. Leon; Frank P. Hoffman

[57] ABSTRACT

Peptide derivatives provided by the present invention are compounds of the general formula

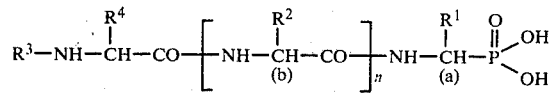

wherein $R^1$ represents a hydrogen atom or the methyl or hydroxymethyl group or a mono-, di- or trihalomethyl mgroup; $R^2$ represents the characterizing group of an α-amino acid of the type normally found in proteins or a lower alkyl or hydroxy- (lower alkyl) group other than the characterising group of an α-amino acid of the type normally found in proteins; $R^3$ represents a lower alkyl, lower cycloalkyl, lower alkenyl, aryl or aryl-(lower alkyl) group; $R^4$ represents a hydrogen atom or a lower alkyl group; n stands for 1,2 or 3; the configuration at the carbon atom designated as (a) is (R) when $R^1$ represents other than a hydrogen atom and the configuration at the carbon atom designated as (b) is (L) when $R^2$ represents other than a hydrogen atom, and pharmaceutically acceptable salts thereof.

The compounds exhibit activity as antibacterial agents against a range of gram-positive and gram-negative bacteria. Also disclosed are intermediates and a process for the production of the end product.

15 Claims, No Drawings

ACYL DERIVATIVES

DESCRIPTION OF THE INVENTION

The present invention relates to peptide derivatives. More particularly, the invention is concerned with peptide derivatives of phosphonic acids, a process for the manufacture thereof and pharmaceutical preparations containing same.

The peptide derivatives provided by the present invention are compounds of the general formula

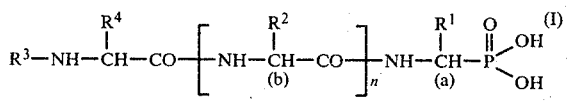

wherein $R^1$ represents a hydrogen atom or the methyl or hydroxymethyl group or a mono-, di- or trihalomethyl group; $R^2$ represents the characterising group of an α-amino acid of the type normally found in proteins or a lower alkyl or hydroxy-(lower alkyl) group other than the characterising group of an α-amino acid of the type normally found in proteins; $R^3$ represents a lower alkyl, lower cycloalkyl, lower alkenyl, aryl or aryl-(lower alkyl) group; $R^4$ represents a hydrogen atom or a lower alkyl group; n stands for 1,2 or 3; the configuration at the carbon atom designated as (a) is (R) when $R^1$ represents other than a hydrogen atom and the configuration at the carbon atom designated as (b) is (L) when $R^2$ represents other than a hydrogen atom, and pharmaceutically acceptable salts thereof.

The term "lower alkyl" is used in this Specification to mean a straight-chain or branched-chain alkyl group which preferably contains up to 8 carbon atoms (e.g. methyl, ethyl, propyl, isopropyl, butyl, tert.butyl, pentyl, hexyl etc). Examples of the aforementioned hydroxy-(lower alkyl) groups are 2-hydroxyethyl, 3-hydroxypropyl, 4-hydroxybutyl etc. The term "lower alkenyl" means a straight-chain or branched-chain alkenyl group which preferably contains from 2 to 8 carbon atoms (e.g. allyl, butenyl etc). Examples of aryl-(lower alkyl) groups are benzyl, phenethyl etc. The term "halo" means fluoro, chloro, bromo or iodo, examples of the aforementioned halomethyl groups being chloromethyl, dichloromethyl, trifluoromethyl etc. The term "the characterising group of an α-amino acid of the type normally found in proteins" means the residue R in a natural α-amino acid of the general formula

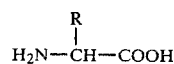

which is of the type normally occurring in proteins. Thus, for example, if the α-amino acid is glycine then R represents a hydrogen atom and if the α-amino acid is alanine then R represents the methyl group. Again, for example, in methionine R represents the 2-methylthioethyl group, in serine R represents the hydroxymethyl group and in tyrosine R represents the p-hydroxybenzyl group. R can also represent a residue which is linked with the amino nitrogen atom (with the loss of one of the hydrogen atoms attached thereto) to form a nitrogen-containing ring as in proline.

When $R^1$ in formula I represents other than a hydrogen atom, the configuration at the carbon atom designated as (a) is (R); that is to say, the configuration which would be obtained by replacing the carboxyl group of a naturally occurring α-amino acid by a phosphorus moiety.

It will be appreciated that the value accorded to $R^2$ in formula I hereinbefore can be the same or different.

Preferred peptide derivatives provided by the present invention are those in which $R^1$ represents the methyl group, as well as those in which both $R^2$'s represent the characterising group of an α-amino acid of the type normally found in proteins or a lower alkyl group other than such a characterising group. Also preferred are peptide derivatives in which $R^3$ represents a lower alkyl group, especially the methyl group.

Examples of compounds of formula I hereinbefore are:

(1R)-1-(N-Sarcosyl-glycyl-L-alanylamino)-ethylphosphonic acid,
(1R)-1-(N-sarcosyl-L-alanyl-L-alanylamino)-ethylphosphonic acid,
(1R)-1-(N-sarcosyl-L-methionyl-L-alanylamino)-ethylphosphonic acid,
(1R)-1-(N-sarcosyl-L-histidyl-L-alanylamino)-ethylphosphonic acid,
(1R)-1-(N-sarcosyl-L-seryl-L-alanylamino)-ethylphosphonic acid,
(1R)-1-(N-sarcosyl-L-tyrosyl-L-alanylamino)-ethylphosphonic acid,
(1R)-1-(N-sarcosyl-L-arginyl-L-alanylamino)-ethylphosphonic acid,
(1R)-1-(N-sarcosyl-L-alanyl-L-arginylamino)-ethylphosphonic acid,
(1R)-1-(N-sarcosyl-L-alanyl-L-serylamino)-ethylphosphonic acid,
(1R)-1-(N-sarcosyl-L-alanyl-L-histidylamino)-ethylphosphonic acid,
(N-sarcosyl-L-alanyl-L-alanylamino)-methylphosphonic acid,
(1R)-1-(N-sarcosyl-L-norvalyl-L-alanylamino)-ethylphosphonic acid,
(1R)-1-(N-sarcosyl-L-alanyl-L-norvalylamino)-ethylphosphonic acid, and
(1R)-1-(N-sarcosyl-L-norvalyl-L-norvalylamino)-ethylphosphonic acid.
(1R)-1-(N-sarcosyl-L-arginyl-L-arginylamino)-ethylphosphonic acid,
(1R)-1-(N-sarcosyl-L-norvalyl-L-arginylamino)-ethylphosphonic acid,
(1R)-1-(N-sarcosyl-glycyl-L-norvalylamino)-ethyl phosphonic acid,
(1R)-1-(N-sarcosyl-L-arginyl-L-norvalylamino)-ethylphosphonic acid,
(1R)-1-(N-sarcosyl-L-valyl-L-norvalylamino)-ethylphosphonic acid,
(1R)-1-(N-sarcosyl-L-alánylamino)-ethylphosphonic acid,
(1R)-1-(N-methyl-L-norvalyl-L-norvalylamino)-ethylphosphonic acid,
(1R)-1-(N-sarcosyl-glycyl-L-norvalyl-L-norvalylamino)-ethylphosphonic acid,
(N-sarcosyl-L-norvalyl-L-norvalylamino)-methylphosphonic acid,
(1R)-1-(N-methyl-L-norvalyl-L-norvalyl-L-norvalylamino)-ethylphosphonic acid,
(1R)-1-(N-ethyl-glycyl-L-alanyl-L-alanylamino)-ethylphosphonic acid,
(1R)-1-(N-(n-propyl)-glycyl-L-alanyl-L-alanylamino)-ethylphosphonic acid, (1R)-1-(N-allyl-glycyl-L-alanyl-L-alanylamino)-ethyl-phosphonic acid, (1R)-1-(N-(n-hexyl)-glycyl-L-alanyl-L-alanylamino)-ethylphosphonic acid, (1R)-1-(N-cyclopropyl-glycyl-L-alanyl-L-alanylamino)-ethylphosphonic acid, (1R)-1-(N-tert.butyl-glycyl-L-alanyl-L-alanylamino)-ethylphosphonic acid, (1R)-1-(N-benzyl-glycyl-L-alanyl-L-alanylamino)-ethylphosphonic acid, (1R)-1-(N-phenyl-glycyl-L-alanyl-L-alanylamino)-ethylphosphonic acid, (1R)-1-(N-methyl-L-alanyl-L-alanyl-L-alanylamino)-ethylphosphonic acid, (1R)-1-(N-methyl-L-valyl-L-valyl-L-norvalylamino)-ethylphosphonic acid, (1R)-1-(N-methyl-L-leucyl-L-norvalyl-L-norvalylamino)-ethylphosphonic acid, (1R)-1-(N-sarcosyl-L-valyl-L-valyl-L-norvalylamino)-ethylphosphonic acid, (1R)-1-(N-methyl-L-valyl-L-norvalyl-L-norvalylamino)-ethylphosphonic acid.

According to the process provided by the invention the peptide derivatives of general formula I hereinbefore and their pharmaceutically acceptable salts are manufactured by (a) cleaving off by methods known per se the protecting group(s) in a compound of the general formula

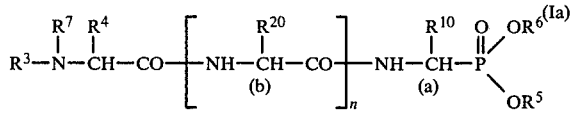

wherein n, $R^3$ and $R^4$ have the significance given earlier; $R^5$ and $R^6$ each represent a hydrogen atom or a lower alkyl protecting group; $R^7$ represents a protecting group; $R^{10}$ has any of the values accorded to $R^1$ hereinbefore or represents a protected hydroxymethyl group; $R^{20}$ has any of the values accorded to $R^2$ hereinbefore except that any amino group present may be in protected form and any other functional group which may be present is in protected form where required; the configuration at the carbon atom designated as (a) is (R) when $R^{10}$ represents other than a hydrogen atom; and the configuration at the carbon atom designated as (b) is (L) when $R^{20}$ represents other than a hydrogen atom, (b) if desired, converting an obtained compound of general formula I into a pharmaceutically acceptable salt.

Compounds of general formula Ia may be manufactured by condensing a compound of the general formula

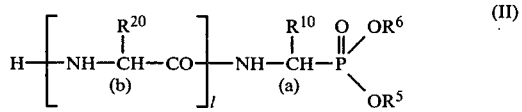

with a compound of the general formula

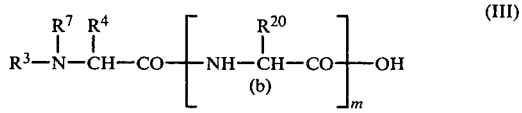

wherein l and m each stand for zero, 1, 2 or 3 with the proviso that the sum of l and m is 1, 2 or 3; and wherein $R^3$, $R^4$, $R^5$, $R^6$, $R^7$, $R^{10}$ and $R^{20}$ are as hereinbefore.

The protecting group denoted by $R^7$ in a compound of formula Ia or III hereinbefore can be any amino-protecting group which is well-known in peptide chemistry. In a preferred embodiment of the process provided by the present invention the amino-protecting group is an aralkoxycarbonyl group, particularly the benzyloxycarbonyl group, or the tert.butoxycarbonyl group. However, the amino-protecting group can also be, for example, a formyl, trityl, trifluoroacetyl or 2-(biphenylyl)-isopropyloxycarbonyl group. An amino group present in $R^{20}$ can be protected in a similar manner. The protecting group present in a protected hydroxymethyl group denoted by $R^{10}$ in a compound of formula II may be any conventional hydroxy-protecting group; for example, an aralkoxycarbonyl group (e.g. the benzyloxycarbonyl group), a lower alkanoyl group (e.g. the acetyl, propionyl and like groups), an aroyl group (e.g. the benzoyl group), a lower alkyl group (e.g. the tert.butyl group) or a lower aralkyl group (e.g. the benzyl group). Any hydroxy group which may be present in $R^{20}$ can be protected with any of the aforementioned hydroxy-protecting groups. Any carboxy group which may be present in $R^{20}$ can be protected with a conventional carboxy-protecting group; for example, a carboxy group can be protected by conversion into an alkyl ester (e.g. the tert.butyl ester) or an aralkyl ester (e.g. the benzyl ester). The protection of any other functional groups present in $R^{20}$ can be carried out in a known manner.

The condensation of a compound of formula II with a compound of formula III can be carried out according to methods known per se in peptide chemistry; for example, according to the mixed anhydride, azide, activated ester, acid chloride, carbodiimide or EEDQ (1-ethoxycarbonyl-2-ethoxy-1,2-dihydroquinoline) method. In a preferred embodiment, a compound of formula II in which l stands for 1, 2 or 3 is condensed with a compound of formua III in which m stands for zero.

In one method, a compound of formula II can be condensed with a compound of formula III in which the carboxy group is a mixed anhydride residue formed with an organic or inorganic acid. Suitably, such a compound of formula III is treated with a tertiary base such as a tri (lower alkyl) amine (e.g. triethylamine) or N-ethylmorpholine in an inert organic solvent (e.g. tetrahydrofuran, 1,2-dimethoxyethane, dichloromethane, toluene, petroleum ether or the like) and the salt obtained is reacted with an appropriate chloroformate (e.g. a lower alkyl chloroformate) at a low temperature. The mixed anhydride thus obtained is then suitably condensed in situ with a compound of formula II.

In another method, a compound of formula II can be condensed with a compound of formula III in which the carboxy group is in the form of an acid azide. This condensation is preferably carried out in an inert organic solvent such as dimethylformamide or ethyl acetate at a low temperature.

In yet another method, a compound of formula II can be condensed with a compound of formula II in which the carboxy group is in the form of an active ester group (e.g. the 4-nitrophenyl, 2,4,5-trichlorophenyl or N-hydroxysuccinimide ester group). This condensation is suitably carried out in an inert solvent such as aqueous dimethylformamide or, where $R^3$ and $R^4$ in a compound of formua III both represent a lower alkoxy group, also in a lower alkanol such as aqueous ethanol.

In a further method, a compound of formula II can be condensed with a compound of formula III in which the carboxy group is in the form of an acid chloride. This condensation is preferably carried out in the presence of a base and at a low temperature. It is also preferred to carry out this condensation in a non-hydrolytic solvent.

In yet a further method, a compound of formula II can be condensed with a compound of formula III in the presence of a carbodiimide (e.g. dicyclohexylcarbodiimide) or EEDQ. This condensation can be carried out in an inert organic solvent (e.g. methylene chloride or a lower alkanol such as methanol, ethanol etc) at room temperature or at a temperature below room temperature.

The condensation of a deprotected compound of formula Ia with a compound of formula III can be carried out in a manner similar to that described for the condensation of compounds II and III.

The cleavage of the protecting group or protecting groups from the condensation product is carried out in accordance with methods known per se; that is to say, methods in actual use for or described in the literature on the cleavage of protecting groups. Thus, for example, an aralkoxycarbonyl group (e.g. benzyloxycarbonyl), the tert.butoxycarbonyl group or the 2-biphenylyl-isopropyloxycarbonyl group can be cleaved off by hydrolysis (e.g. by treatment with hydrogen bromide in glacial acetic acid). An aralkoxycarbonyl group (e.g. benzyloxycarbonyl) can also be cleaved off by hydrogenolysis (e.g. in the presence of palladium-on-charcoal or platinum oxide). The tert.butoxycarbonyl or 2-biphenylyl-isopropyloxycarbonyl group can also be cleaved off using hydrogen chloride in dioxan. A trityl group can be cleaved off, for example, by treatment with dilute acetic acid. When the condensation product contains a 2-methylthioethyl group $R^{20}$ and an aralkoxycarbonyl protecting group (e.g. benzyloxycarbonyl), the cleavage of said protecting group is advantageously carried out in the presence of diethyl phosphite or methyl ethyl sulphide. Lower alkyl protecting groups denoted by $R^5$ and $R^6$ can be cleaved off by treatment with hydrogen bromide in glacial acetic acid or using trimethylchlorosilane or trimethylbromosilane followed by aqueous hydrolysis. It will be appreciated that where more than one protecting group is present the cleavage of the protecting groups can be carried out in a single step or in more than one step depending on the nature of said groups. However, it is preferred to use protecting groups which can be cleaved off in a single step.

Compounds of formula I hereinbefore are amphoteric and form pharmaceutically acceptable salts with pharmaceutically acceptable strong acids (e.g. hydrochloric acid, hydrobromic acid, sulphuric acid, methanesulphonic acid, paratoluenesulphonic acid etc.) and bases (e.g. sodium hydroxide, potassium hydroxide etc).

The compounds of formula II in which l stands for zero are known or can be prepared in analogy to the preparation of known compounds.

The compounds of formula II in which l stands for 1 can be prepared by condensing a compound of formula II in which l stands for zero with a compound of the general formula

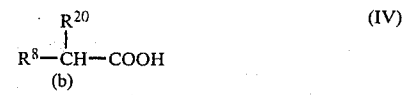

wherein $R^{20}$ has the significance given earlier; $R^8$ represents a protected amino group; and the configuration at the carbon atom designated as as (b) is as defined earlier, and cleaving off the protecting group present in $R^8$ in the condensation product and also, if desired, any other protecting group or groups which may be present in said product.

The compounds of formula II in which l stands for 2 can be prepared by condensing a compound of formula II in which l stands for zero or 1 with a compound of the general formula

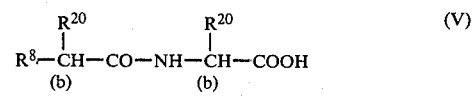

wherein $R^8$ and $R^{20}$ have the significance given earlier; and the configuration at the carbon atoms designated as (b) is as defined earlier, in the case where l stands for zero or with a compound of formula IV in the case where l stands for 1 and cleaving off the protecting group present in $R^8$ in the condensation product and also, if desired, any other protecting group or groups which may be present in said product.

The compounds of formula II in which l stands for 3 can be produced in an analogous manner.

The protected amino group denoted by $R^8$ can carry a protecting group of the kind mentioned earlier in connection with $R^7$. In addition, the protected amino group denoted by $R^8$ can be the phthalimido group.

The aforementioned condensation involving a compound of formula IV or V can be carried out in a manner analogous to that described earlier in connection with the condensation of a compound of formula II with a compound of formula III.

The cleavage of the protecting group or groups from the resulting condensation product can be carried out in a manner analogous to that described earlier in connection with the cleavage of the protecting group or groups from the product obtained by condensing a compound of formula II with a compound of formula III. When $R^8$ in the condensation product represents the phthalimido group, then $R^8$ can be converted into the amino group by hydrazinolysis.

The compounds of formulae III, IV and V hereinbefore are either known or can be prepared in analogy to the preparation of known compounds.

The compounds of formula II in which l stands for 2 or 3 and at least one $R^{20}$ represents a lower alkyl or hydroxy-(lower alkyl) group other than the characterising group of an amino acid of the type normally found in proteins or such a hydroxy-(lower alkyl) group in which the hydroxy moiety is protected are novel and also form part of the present invention.

Preferred among the aforementioned novel compounds of formula II are those in which $R^5$ and $R^6$ each represent a hydrogen atom. Also preferred are those novel compounds of formula II in which $R^{10}$ represents the methyl group as well as those in which at least one $R^{20}$ represents a lower alkyl group, especially the ethyl, n-propyl or n-butyl group.

Examples of the novel compounds of formula II are:
(1R)-1-(L-Norvalyl-L-alanylamino)-ethylphosphonic acid,
(1R)-1-(L-alanyl-L-norvalylamino)-ethylphosphonic acid,
(1R)-1-(L-norvalyl-L-norvalylamino)-ethylphosphonic acid,
(1R)-1-(glycyl-L-norvalylamino)-ethylphosphonic acid,
(1R)-1-(L-valyl-L-norvalylamino)-ethylphosphonic acid,
(1R)-1-(glycyl-L-norvalyl-L-norvalylamino)-ethylphosphonic acid,
(1R)-1-(L-valyl-L-valyl-L-norvalylamino)-ethylphosphonic acid and
(L-norvalyl-L-norvalylamino)-methylphosphonic acid.

The peptide derivatives provided by the present invention possess an antibacterial activity against a wide range of gram-positive and gram-negative bacteria such as *Escherichia coli, Serratia marcescens, Klebsiella aerogenes, Streptococcus faecalis* and *Haemophilus influenzae*. They possess particularly good activity against *Streptococcus faecalis* and *Haemophilus influenzae*, both in vivo and in vitro.

The peptide derivatives provided by the present invention can be used as medicaments; for example, in the form of pharmaceutical preparations which contain them in association with a compatible pharmaceutical carrier material. This carrier material can be an organic or inorganic carrier material which is suitable for enteral (e.g. oral) or parenteral administrations. Examples of such carrier materials are water, gelatin, lactose, starches, magnesium stearate, talc, vegetable oils, gum arabic, polyalkyleneglycols, petroleum jelly etc. The pharmaceutical preparations can be made up in a solid form (e.g. as tablets, dragees, suppositories or capsules) or in a liquid form (e.g. as solutions, suspensions or emulsions). The pharmaceutical preparations may be subjected to conventional pharmaceutical operations such as sterilisation and may contain adjuvants such as preserving agents, stabilising agents, wetting agents, emulsifying agents, salts for varying the osmotic pressure of buffers. When a buffer is used, the pH of the pharmaceutical preparation will, of course, vary within a range which is well-known in pharmaceutical practice.

The daily dosage of peptide derivatives administered to adults will vary within wide limits depending on factors such as the particular peptide derivative chosen, the route of administration and the infection to be treated. For example, a daily dosage for oral administration may amount to about 2000 mg to 4000 mg and a daily dosage for parenteral administration may amount to about 800 mg to 2000 mg. It will be appreciated that daily dosages can be administered in a single dosage or in divided dosages and that the dosages mentioned earlier may be varied upwards or downwards according to individual requirements and fitted to the exigencies of a particular situation as determined by the prescribing physician.

The following Examples illustrate the process provided by the present invention:

EXAMPLE 1

(A) The Preparation of the Starting Material (i) 26.7 g (0.3 mol) of sarcosine were dissolved in 150 m (0.3 mol) of 2-N sodium hydroxide. The resulting solution was stirred at 0° C. while 75 ml of 4-N sodium hydroxide and 51.3 ml (ca 360 mmol) of benzyl chloroformate were added alternately and portionwise over a period of 0.5 hour, the temperature being held below 5° C. The mixture was stirred for a further 1 hour while the temperature was allowed to rise to room temperature. The mixture was then extracted with two 300 ml portions of diethyl ether. The aqueous layer was separated, cooled to 0° C. and, while stirring, made acid to Congo red with ca 25 ml of concentrated hydrochloric acid. The mixture was stirred for 1 hour while allowing the temperature to rise to room temperature. The mixture was then extracted with three 300 ml portions of diethyl ether, the combined extracts were dried over sodium sulphate and evaporated to give ca 64 g of N-benzyloxycarbonyl-sarcosine in the form of an oil.

(ii) 16 g (ca 72 mmol) of N-benzyloxycarbonyl-sarcosine were dissolved in 150 ml of dimethoxyethane. The solution was cooled to 0° C. and treated successively with 8.28 g (72 mmol) of N-hydroxysuccinimide and 16.3 g (72 mmol) of dicyclohexylcarbodiimide. The mixture was then stirred at 4° C. for 16 hours. The solid byproduct was filtered off and the filtrate was evaporated to give an oil. This oil, N-benzyloxycarbonyl-sarcosine N-hydroxysuccinimide ester, was dissolved in dimethylformamide and a small amount of insoluble solid was filtered off. The filtrate was diluted with dimethylformamide to a total volume of 100 ml in a volumetric flask and stored at 4° C. until used, this solution being referred to hereinafter as the stock solution.

(B) THE PROCESS (i) 4 g (15 mmol) of (1R)-1-(L-alanyl-L-alanylamino)-ethylphosphonic acid were dissolved in a mixture of 15 ml of water and 4.2 ml (30 mmol) of triethylamine and the solution was stirred at 0° C. while 30 ml of the aforementioned stock solution of N-benzyloxycarbonyl-sarcosine N-hydroxysuccinimide ester were added. The mixture was stirred at 0° C. for 1 hour and then at room temperature for 16 hours. A small amount of solid was filtered off and washed with 10 ml of water/dimethylformamide (1:2). The filtrate and washings were combined and evaporated under an oil-pump vacuum. The residual gum was dissolved in 45 ml of water-methanol (1:2) and passed down a column of cation exchange resin [B.D.H., Zerolit 225, SRC 13, $RSO_3H$; 100 g; freshly regenerated in the acid cycle and made up in water/methanol (1:2)]. Elution with water/methanol (1:2) yielded an acid eluate of ca 400 ml which was evaporated. The residual solid was partitioned between 200 ml of water and 100 ml of methylene chloride. The aqueous layer was re-extracted with 50 ml of methylene chloride and the solvent extracts were back-washed separately with 100 ml of water. The combined aqueous extracts were titrated to pH 4.5 with 1-N-aqueous benzylamine and evaporated to give a solid. Recrystallisation of this solid from 100 ml of water with refrigeration followed by filtration and washing with water and then with acetone gave 5.37 g of the monobenzylamine salt of (1R)-1-[(N-benzyloxycarbonyl-sarcosyl-L-alanyl-)amino]-ethylphosphonic acid of melting point 246°–247° C. (decomposition); $[\alpha]_D^{20} = -79.1°$ (c=0.5% in water); $[\alpha]_{365}^{20} = -277°$ (c=0.5% in water). Evaporation of the filtrate and recrystallisation of the residue from 40 ml of water gave a further 1.687 g of the desired monobenzylamine salt of melting point 244°–246° C. (decomposition). The total yield amounted to 7.057 g (81%).

(ii) 7 g (12 mmol) of the monobenzylamine salt of (1R)-1-[(N-benzyloxycarbonyl-sarcosyl-L-alanyl-L-alanyl)amino]-ethylphosphonic acid were dissolved in a mixture of 100 ml of warm water and 20 ml of 2-N ammonium hydroxide. The solution was passed down a column of cation exchange resin (B.D.H., Zerolit 225, SRC 13, RSO$_3$H; 100 g; freshly regenerated in the acid cycle). Elution was carried out with water. To the aqueous acid eluate were added 0.2 g of 10% palladium-on-charcoal catalyst, 6 drops of glacial acetic acid and an amount of ethanol equal in volume to the aqueous eluate. The mixture was hydrogenated at room temperature and atmospheric pressure. The catalyst was filtered off and the solvents were removed by evaporation. The resulting white solid was recrystallised from a mixture of 50 ml of water and 50 ml of ethanol to give a first crop of 3.5 g (86%) of product of melting point 300°–310° C. (decomposition). Evaporation of the filtrate and recrystallisation of the residue from a mixture of 20 ml of water and 20 ml of ethanol gave a second crop of 0.29 g of product of melting point 302°–303° C. (decomposition). The total yield was 3.79 g (93%). Both crops were combined and recrystallised from a mixture of 125 ml of water and 125 ml of ethanol to give 3.385 g of (1R)-1-(N-sarcosyl-L-alanyl-L-alanylamino)-ethylphosphonic acid of melting point 306°–307° C. (decomposition); $[\alpha]_D^{20} = -118°$ (c=0.5% in water). Evaporation of the filtrate and recrystallisation of the residue from a mixture of 12 ml of water and 24 ml of ethanol gave a further 0.16 g of product of melting point 305°–306° C. (decomposition). The total yield of recrystallised product was 3.545 g (87%).

EXAMPLE 2

(i) In a manner analogous to that described in Example 1 (B) (i), from 40 ml of the stock solution of N-benzyloxycarbonylsarcosine N-hydroxysuccinimide ester referred to in Example 1 (A) (ii) and 5.06 g (20 mmol) of (1R)-1-(glycyl-L-alanylamino)-ethylphosphonic acid there were obtained, after titration with benzylamine, evaporation and trituration with acetone, 10.7 g (95%) of crude product of melting point ca 195°–205° C. (decomposition). This product was recrystallised from a mixture of 80 ml of water, 200 ml of ethanol and 640 ml of diethyl ether to give 7.33 g (65%) of the monobenzylamine salt of (1R)-1-[(N-benzyloxycarbonyl-sarcosyl-glycyl-L-alanyl)amino]-ethylphosphonic acid of melting point 222°–224° C. (decomposition); $[\alpha]_D^{20} = -43.1°$ (c=0.5% in water); $[\alpha]_{365}^{20} = -155°$ (c=0.5% in water). The filtrate from the foregoing recrystallisation was evaporated to give a further ca 4.5 g of the desired monobenzylamine salt of melting point 220°–224° C. (decomposition).

(ii) In a manner analogous to that described in Example 1 (B) (ii), but dissolving in water alone prior to the ion exchange, from 4 g (7.5 mmol) of the monobenzylamine salt of (1R)-1-[(N-benzyloxycarbonyl-sarcosyl-glycyl-L-alanyl)amino]-ethyl-phosphonic acid there were obtained, after evaporation with n-propanol followed by recrystallisation from a mixture of 15 ml of water and 30 ml of ethanol, 1.36 g (56%) of (1R)-1-(N-sarcosyl-glycyl-L-alanylamino)-ethylphosphonic acid of melting point 291°–292° C. (decomposition); $[\alpha]_D^{20} = -77.9°$ (c=0.5% in water); $[\alpha]_{365}^{20} = -285°$ (c=0.5% in water).

EXAMPLE 3

(i) In a manner analogous to that described in Example 1 (B) (i), from 30 ml of the stock solution of N-benzyloxycarbonyl-sarcosine N-hydroxysuccinimide ester referred to in Example 1(A) (ii) and 3.795 g (15 mmol) of (L-alanyl-L-alanyl-amino)-methylphosphonic acid there were obtained, after trituration with acetone, 8.39 g of crude product of melting point 228°–230° C. (decomposition). Recrystallisation from 75 ml of water gave 6.2 g (73%) of the monobenzylamine salt of [(N-benzyloxycarbonyl-sarcosyl-L-alanyl-L-alanyl)amino]-methylphosphonic acid of melting point 235°–236° C. (decomposition); $[\alpha]_D^{20} = -61.7°$ (c=1% in water); $[\alpha]_{365}^{20} = -215°$ (c=1% in water).

(ii) 5.65 g (10 mmol) of the monobenzylamine salt of [(N-benzyloxycarbonyl-sarcosyl-L-alanyl-L-alanyl)amino]-methylphosphonic acid were dissolved in a mixture of 75 ml of water, 75 ml of methanol and 2 ml of concentrated hydrochloric acid. 0.5 g of 10% palladium-on-charcoal catalyst was added. The mixture was hydrogenated at room temperature and atmospheric pressure. The catalyst was filtered off and the solvents were removed by evaporation. The residual solid was extracted with 50 ml of methanol and filtered, and the solid was washed with two 10 ml portions of methanol and dried to give a first crop of 1.387 g of product of melting point 245°–253° C. (decomposition). The combined filtrates were treated with 3 ml of propylene oxide, a white solid precipitating. The mixture was left to stand at room temperature for 2 hours and then in a refrigerator overnight. The resulting solid was filtered off, washed with methanol and dried to give a second crop of 1.81 g of product of melting point 284°–285° C. (decomposition). The first crop was dissolved in a mixture of 50 ml of water and 50 ml of methanol and the solution was treated with 3 ml of propylene oxide to a permanent pH of ca 5. The solution was evaporated and the resulting solid was triturated with 50 ml of methanol and left to stand under methanol overnight. The solid was subsequently filtered off and dried to give 1.21 g of product of melting point 285°–286° C. (decomposition). This latter product was combined with the second crop referred to earlier and recrystallised from a mixture of 35 ml of water and 35 ml of ethanol to give 2.76 g (85%) of (N-sarcosyl-L-alanyl-L-alanylamino)-methylphosphonic acid of melting point 294°–295° C. (decomposition); $[\alpha]_D^{20} = -78.7°$ (c=0.5% in water); $[\alpha]_{365}^{20} = -277°$ (c=0.5% in water).

EXAMPLE 4

(A) THE PREPARATION OF THE STARTING MATERIAL 5.88 g (30 mmol) of (1R)-1-(L-alanylamino)-ethylphosphonic acid were dissolved in 50 ml of water and to the stirred solution were added 6.06 g (60 mmol) of triethylamine followed by 50 ml of dimethylformamide. The solution was cooled to 0° C. and 12.5 g (36 mmol) of tertbutoxycarbonyl-L-methionine N-hydroxysuccinimide ester were added in the form of a solid in a single portion, the ester being washed in with 50 ml of dimethylformamide. The mixture was stirred at 0° C. for 2 hours and then at room temperature overnight. Subsequently, the mixture was evaporated to dryness under an oil-pump vacuum, the residue was taken up in 150 ml of water and a small amount of solid was filtered off. The filtrate was acidified with 10 ml of concentrated hydrochloric acid and the solution was extracted with 100 ml of diethyl ether. The solvent extract was back-washed with 75 ml of water and the aqueous layers were combined, left to stand at room temperature for 2 days and then evaporated to give an oil. This oil was dissolved in 100 ml of ethanol, the solution was stirred and then treated with two 5 ml portions of propylene oxide up to a permanent pH of ca 5 to moist pH paper. The solution became a gelatinous mass which was left to stand at room temperature overnight. Filtration yielded a solid which was washed with 50 ml of ethanol, there being obtained 13.2 g of crude product of melting point 220°–228° C. (decomposition). Recrystallisation from a mixture of 1 litre of water and 1 litre of ethanol gave 8.17 g of (1R)-1-(L-methionyl-L-alanylamino)-ethylphosphonic acid of melting point 250°–252° C. (decomposition); $[\alpha]_D^{20} = -35.6°$ (c=0.5% in 1-N-sodium hydroxide); $[\alpha]_{365}^{20} = -136°$ (c=0.5% in 1-N sodium hydroxide). Evaporation of the filtrate and recrystallisation of the residue from a mixture of 250 ml of water and 500 ml of ethanol gave a further 1.22 g of melting point 250°–252° C. (decomposition). The total yield was 9.39 g (95%).

(B) THE PROCESS (i) In a manner analogous to that described in Example 1 (B) (i), but extracting the residue obtained after evaporating the acid eluate from the ion exchange step with diethyl ether rather than partitioning same between water and methylene chloride, from 29 ml of the stock solution of N-benzyloxycarbonyl-sarcosine N-hydroxysuccinimide ester referred to in Example 1(A) (ii) and 2.4 g (7.3 mmol) of (1R)-1-(L-methionyl-L-alanylamino)-ethylphosphonic acid there were obtained, after trituration with 100 ml of acetone, 4.07 g of crude product of melting point 218°–222° C. (decomposition). Recrystallisation from a mixture of 400 ml of methanol and 400 ml of diethyl ether gave, as a gelatinous precipitate, 3.54 g (76%) of the monobenzylamine salt of (1R)-1-[(N-benzyloxycarbonyl-sarcosyl-L-methionyl-L-alanyl)amino]-ethylphosphonic acid of melting point 231°–234° C. (decomposition); $[\alpha]_D^{20} = -28.6°$ (c=0.6% in acetic acid); $[\alpha]_{365}^{20} = -111°$ (c=0.6% in acetic acid).

(ii) 3.76 g (5.9 mmol) of the monobenzylamine salt of (1R)-1-[(N-benzyloxycarbonyl-sarcosyl-L-methionyl-L-alanyl)amino]-ethylphosphonic acid were stirred at room temperature for 5 hours with a mixture of 6 ml of diethyl phosphite and 12 ml of a 45% solution of hydrogen bromide in glacial acetic acid. 75 ml of diethyl ether were added to precipitate a gum which was washed by decantation with 75 ml of diethyl ether. The gum remaining was taken up in 75 ml of methanol while stirring. Three 5 ml portions of propylene oxide were added to give a gelatinous solid which was difficult to stir. The mixture was left to stand for 1 hour and then filtered. The residue was washed with methanol and with diethyl ether and then dried to give 2.05 g of a gum-like solid. Recrystallisation from a mixture of 80 ml of water (some insoluble material being filtered off) and 400 ml of ethanol gave, as a gelatinous precipitate, a first crop of product weighing 0.53 g and melting at 262°–265° C. (decomposition). Evaporation of the mother liquors and recrystallisation of the residue from a mixture of 30 ml of water and 180 ml of ethanol gave a second crop of product weighing 0.16 g and melting at 262°–264° C. (decomposition). Recrystallisation of the first crop from a mixture of 30 ml of water and 120 ml of ethanol gave (1R)-1-(N-sarcosyl-L-methionyl-L-alanylamino)-ethylphosphonic acid of melting point 276°–278° C. (decomposition); $[\alpha]_D^{20} = -56.0°$ (c=0.48% in freshly prepared 1-N-sodium hydroxide); $[\alpha]_{365}^{20} = -217°$ (c=0.48% in freshly prepared 1-N-sodium hydroxide).

EXAMPLE 5

(A) THE PREPARATION OF THE STARTING MATERIAL (i) 9.1 g (20 mmol) of $N^{\alpha},N^{im}$-bis(N-benzyloxycarbonyl)-L-histidine were dissolved in 100 ml of dimethoxyethane and to the stirred solution were added 2.30 g (20 mmol) of N-hydroxysuccinimide. The solution was cooled to 0° C. and 4.53 g (22 mmol) of dicyclohexylcarbodiimide were added. The mixture was stirred at 0° C. for 2 hours and then stored at 0° C. overnight. The precipitate was filtered off and the filtrate was evaporated to give a gum. This gum, $N^{\alpha}, N^{im}$-bis(N-benzyloxycarbonyl)-L-histidine N-hydroxysuccinimide ester, was dissolved in 40 ml of dimethylformamide and the resulting solution was used in the next step.

(ii) 3.14 g (16 mmol) of (1R)-1-(L-alanylamino)-ethylphosphonic acid were condensed with the aforementioned solution of $N^{\alpha},N^{im}$-bis(N-benzyloxycarbonyl)-L-histidine N-hydroxysuccinimide ester in a manner analogous to that described in Example 1(B) (i). After working-up in the normal manner, there was obtained (1R)-1-[(N-benzyloxycarbonyl-L-histidyl-L-alanyl)amino]-ethylphosphonic acid of melting point 256°–258° C. (decomposition).

(iii) 3.27 g (7 mmol) of (1R)-1-[(N-benzyloxycarbonyl-L-histidyl-L-alanyl)amino]-ethylphosphonic acid were ground to a powder and then stirred vigorously at room temperature for 6 hours with a mixture of 15 ml of 45% hydrogen bromide in glacial acetic acid and 5 ml of glacial acetic acid. 75 ml of diethyl ether were added to precipitate a gum which was washed by decantation with a further 75 ml of diethyl ether. The residual gum was dissolved in 50 ml of methanol and two 3 ml portions of propylene oxide were added to the stirred solution to give a solid. The mixture was left to stand overnight and the solid was then filtered off and washed successively with methanol and diethyl ether to give 2.47 g of crude product of melting point 220°–230° C. (decomposition). Recrystallisation from a mixture of 50 ml of water and 125 ml of ethanol gave 2.02 g (87%) of (1R)-1-(L-histidyl-L-alanylamino)-ethylphosphonic acid of melting point 242°–245° C. (decomposition); $[\alpha]_{365}^{20} = -166°$ (c=0.5% in water).

(B) THE PROCESS (i) In a manner analogous to that described in Example 1 (B) (i), 27 ml of the stock solution of N-benzyloxycarbonyl-sarcosine N-hydroxysuccinimide ester referred to in Example 1 (A) (ii) were condensed with 3 g (9.0 mmol) of (1R)-1-(L-histidyl-L-alanylamino)-ethylphosphonic acid. After standing at room temperature for 16 hours, the mixture had set to an almost solid mass. 200 ml of water were added and the resulting mixture was then stirred and filtered. The filtrate was evaporated under an oil-pump vacuum (0.1 mm Hg) to give a solid which was triturated with 150 ml of acetone, left to stand at room temperature for 0.5 hour and subsequently filtered to give 4.6 g (95%) of product of melting point 238°–240° C. (decomposition). Recrystallisation of a sample of this product from 10 ml of hot water gave (1R)-1-[(N-benzyloxycarbonyl-sarcosyl-L-histidyl-L-alanyl)amino]-ethylphosphonic acid of melting point 243°–245° C. (decomposition); $[\alpha]_D^{20} = -44.1°$ (c=0.46% in freshly prepared 0.1-N sodium hydroxide); $[\alpha]_{365}^{20} = -182°$ (c=0.46% in freshly prepared 0.1-N sodium hydroxide).

(ii) In a manner analogous to that described in part (A) (iii) of this Example, from 4 g (7.4 mmol) of (1R)-1-[(N-benzyloxycarbonyl-sarcosyl-L-histidyl-L-alanyl)amino]-ethylphosphonic acid there were obtained 2.82 g of crude product of melting point 276°–278° C. (decomposition). Recrystallisation from a mixture of 30 ml of water and 60 ml of ethanol gave 2.47 g (69%) of the monohydrobromide salt of (1R)-1-(N-sarcosyl-L-histidyl-L-alanylamino)-ethylphosphonic acid of melting point 280°–281° C. (decomposition); $[\alpha]_D^{20} = -48.2°$ (c=0.5% in water); $[\alpha]_{365}^{20} = -179°$ (c=0.5% in water).

EXAMPLE 6

(A) THE PREPARATION OF THE STARTING MATERIAL (i) 6.2 g (14.7 mmol) of $N^\alpha$, $N^{im}$-bis(N-benzyloxycarbonyl)-L-histidine were converted into the N-hydroxysuccinimide ester in a manner analogous to that described in Example 1(A) (ii). The resulting active ester (ca 14.7 mmol) was dissolved in 25 ml of dimethylformamide and the resulting solution was rapidly added dropwise at 0° C. to a stirred solution of B 1.5 g (12 mmol) of (1R)-1-aminoethylphosphonic acid in a mixture of 25 ml of water, 25 ml of dimethylformamide and 2.4 g of triethylamine. The mixture was stirred at 0° C. for 2 hours and then at room temperature overnight. A small amount of solid was filtered off, the filtrate was evaporated under an oil-pump vacuum and the residue was re-evaporated firstly with water and then with n-propanol. There were obtained 11.6 g of residue. This residue was triturated with 100 ml of acetone to give a white crystalline precipitate which was filtered off and washed with 50 ml of acetone. There were obtained 4.02 g (85%) of substantially pure (1R)-1-[N$^\alpha$-benzyloxycarbonyl-L-histidyl)amino]-ethylphosphonic acid of melting point 236°–239° C. (decomposition); $[\alpha]_D^{20} = -18.2°$ (c=0.49% in acetic acid). Recrystallisation of a sample from water, ethanol and diethyl ether gave (1R)-1-[N$^\alpha$-benzyloxycarbonyl-L-histidyl)amino]-ethylphosphonic acid of melting point 244°–246° C. (decomposition); $[\alpha]_D^{20} = -18.6°$ (c=0.37% in acetic acid).

(ii) 7.2 g (18.2 mmol) of (1R)-1-[N$^\alpha$-benzyloxycarbonyl-L-histidyl)amino]-ethylphosphonic acid were dissolved in a mixture of 50 ml of glacial acetic acid and 50 ml of water and 1 g of 10% palladium-on-charcoal catalyst was added to the solution. The resulting mixture was hydrogenated overnight at room temperature and pressure. The catalyst was removed by filtration, the filtrate was evaporated and the residue was re-evaporated three times with water and then with n-propanol. The resulting solid was triturated with 60 ml of methanol and filtered to give 4.17 g of crude product of melting point 180° C. Recrystallisation from a mixture of 70 ml of water and 105 ml of ethanol gave 3.75 g (79%) of slightly hygroscopic (1R)-1-(L-histidylamino)-ethylphosphonic acid of melting point 185° C. (decomposition); $[\alpha]_D^{20} = -120°$ (c=0.36% in water).

(iii) In a manner analogous to that described in Example 1 (B) (i), 7.2 g (22.5 mmol) of N-benzyloxycarbonyl-L-alanine N-hydroxysuccinimide ester were condensed with B 3.93 g (15 mmol) of (1R)-1-(L-histidylamino)-ethylphosphonic acid. After filtration, the mixture was evaporated to give an oil. Trituration of this oil with 150 ml of acetone gave 6.28 g of crude product of melting point ca 150° C. Recrystallisation of a sample of this crude product from water, ethanol and diethyl ether gave (1R)-1-[(N-benzyloxycarbonyl-L-alanyl-L-histidyl)amino]-ethylphosphonic acid of melting point 253°–255° C. (decomposition); $[\alpha]_D^{20} = -44.1°$ (c=0.5% in water); $[\alpha]_{365}^{20} = -152°$ (c=0.5% in water).

(iv) In a manner analogous to that described in Example 5 (A) (iii), from 5.87 g (12.6 mmol) of (1R)-1-[(N-benzyloxycarbonyl-L-alanyl-L-histidyl)amino]-ethylphosphonic acid there were obtained 4.59 g of crude product of melting point 197° C. (decomposition). Recrystallisation from a mixture of 25 ml of water (with filtration) and 100 ml of ethanol gave 1.68 g (40%) of (1R)-1-(L-alanyl-L-histidylamino)-ethylphosphonic acid of melting point 202° C. (decomposition); $[\alpha]_D^{20} = -37.3°$ (c=0.5% in water); $[\alpha]_{365}^{20} = -148°$ (c=0.5% in water).

(B) The Process (i) In a manner analogous to that described in Example 1 (B) (i), from 18 ml of the stock solution of N-benzyloxylcarbonyl-sarcosine referred to in Example 1(A) (ii) and 2 g (6 mmol) of (1R)-1-(L-alanyl-L-histidylamino)-ethylphosphonic acid there were obtained, after trituration with acetone, 2.57 g of essentially pure (1R)-1-[(N-benzyloxycarbonyl-sarcosyl-L-alanyl-L-histidyl)amino]-ethylphosphonic acid of melting point 256° C. (decomposition).

(ii) In a manner analogous to that described in Example 5 (A) (iii), from 2.5 g (4.6 mmol) of (1R)-1-[(N-benzyloxycarbonyl-sarcosyl-L-alanyl-histidyl)amino]-ethylphosphonic acid there were obtained 2.25 g of crude product of melting point 187° C. Recrystallisation from a mixture of 25 ml of water (with filtration) and 150 ml of ethanol gave 1.20 g of (1R)-1-(N-sarcosyl-L-alanyl-L-histidylamino)-ethylphosphonic acid of melting point 250° C. (decomposition); $[\alpha]_D^{20} = -58.6°$ (c=0.5% in water); $[\alpha]_{365}^{20} = -214°$ (c=0.5% in water).

EXAMPLE 7

(A) The Preparation Of The Starting Material (i) (a) 10.6 g (30 mmol) of N-benzyloxycarbonyl-L-nitroarginine suspended in 500 ml of petroleum ether were stirred with 3.03 g (30 mmol) of triethylamine and the mixture was cooled to $-5°$ C. 4.11 g (30 mmol) of isobutyl chloroformate were added dropwise and the mixture obtained was held at $-5°$ C. for 0.5 hour. The resulting mixed anhydride was rapidly treated dropwise while stirring at $-5°$ C. with a solution of 3.75 g (30 mmol) of (1R)-1-aminoethylphosphonic acid in 50 ml of water containing 6.06 g (60 mmol) of triethylamine. The mixture was stirred at $-5°$ C. for a further 2 hours and then at room temperature overnight. 150 ml of water were added and the phases were separated. The aqueous phase was evaporated to dryness and the residue was taken up in a mixture of 50 ml of water and 50 ml of methanol. The solution was passed down a column of cation exchange resin (B.D.H., Zerolit 225, SRC 13, RSO$_3$H; 150 g). The column was eluted with water/methanol (1:1), the acid eluate was evaporated to dryness and the residue was re-evaporated with water. The gum-like residue was partitioned between 150 ml of water and 100 ml of ethyl acetate and the ethyl acetate extract was back-washed with 100 ml of water. Further extraction with two 100 ml portions of water gave a second combined aqueous extract. The aqueous extracts were evaporated, the residue was dissolved in water/methanol (1:1) and the solution was titrated to pH 4.5 with 4-N-aqueous benzylamine. Evaporation and crystallisation of the residue from methanol/diethyl ether gave 4.12 g of the monobenzylamine salt of (1R)-1-[(N-benzyloxycarbonyl-L-nitroarginyl)amino]-ethylphosphonic acid of melting point 214°–217° C. (decomposition); $[\alpha]_D^{20} = -16.4°$ (c=0.52% in methanol).

(i) (b) 26.5 g (75 mmol) of N-benzyloxycarbonyl-L-nitroarginine were dissolved in 200 ml of dimethylformamide and to the stirred solution were added 8.6 g (75 mmol) of N-hydroxy-succinimide. The resulting solution was cooled to 0° C. and treated with 17 g (82.5 mmol) of dicyclohexylcarbodiimide. The mixture obtained was stirred at 0° C. for 2 hours and then at room temperature overnight. The mixture was cooled to 0° C. and the solid byproduct was filtered off. The filtrate was evaporated under an oil-pump vacuum to give a pale yellow oil, N-benzyloxycarbonyl-L-nitroarginine N-hydroxysuccinimide ester, which was dissolved in 60 ml of dimethylformamide and added rapidly at 0° C. to a solution of 7.8 g (62.5 mmol) of (1R)-1-aminoethylphosphonic acid in a mixture of 60 ml of water, 12.6 g of trimethylamine and 60 ml of dimethylformamide. The mixture was stirred at 0° C. for several hours and then at room temperature overnight. A small amount of solid was filtered off and the filtrate was evaporated to dryness under an oil-pump vacuum at a bath temperature of 35° C. The residual oil was triturated with 100 ml of methanol to give a white solid which was filtered off. The filtrate was diluted with 50 ml of water and the solution was passed down a column of cation exchange resin (RSO₃H; 300 g). Elution of the column with methanol/water (2:1) yielded an acid eluate of 750 ml which was evaporated. The residue was partitioned between 300 ml of water and 150 ml of ethyl acetate and the organic layer was further extracted with 100 ml of water. The total aqueous extracts were back-washed with 100 ml of ethyl acetate. The combined ethyl acetate extracts were back-washed with two 150 ml portions of water. The combined aqueous extracts were treated with benzylamine as described in the preceding paragraph to give 11.54 g of the monobenzylamine salt of (1R)-1-[(N-benzyloxycarbonyl-L-nitroarginyl)amino]-ethylphosphonic acid of melting point 209°–212° C. (decomposition).

(ii) 4 g (7 mmol) of the monobenzylamine salt of (1R)-1-[(N-benzyloxycarbonyl-L-nitroarginyl)amino]-ethylphosphonic acid were added to 10 ml of a 45% solution of hydrogen bromide in glacial acetic acid and washed in with 3 ml of glacial acetic acid. The mixture was stirred at room temperature for 6 hours and then 75 ml of diethyl ether were added to precipitate a gum. The supernatant was removed by decantation and the gum was washed with a further 75 ml of diethyl ether. The gum was dissolved in 40 ml of methanol and the stirred solution was treated with 5 ml of propylene oxide to give a white precipitate after 5 minutes. The mixture was stirred at room temperature for 1 hour until the supernatant had a pH of 3 to moist pH paper. A further 3 ml of propylene oxide were then added and the mixture was left to stand overnight. The separated solid was filtered off and washed with methanol and then with diethyl ether to give 2.19 g (95%) of (1R)-1-(L-nitroarginylamino)-ethylphosphonic acid of melting point 240°–243° C. (decomposition); $[\alpha]_D^{20} = -13.2°$ (c=0.51% in water).

(iii) 11.5 g (36 mmol) of N-benzyloxycarbonyl-L-alanine N-hydroxysuccinimide ester were condensed with 8 g (24.5 mmol) of (1R)-1-(L-nitroarginylamino)-ethylphosphonic acid in a manner analogous to that described in the first paragraph of this Example. Working-up as described in said paragraph gave 13.92 g of monobenzylamine salt of melting point 210°–215° C. (decomposition). Recrystallisation of a sample from a mixture of water, ethanol and diethyl ether gave the monobenzylamine salt of (1R)-1-[(N-benzyloxycarbonyl-L-alanyl-L-nitroarginyl)amino]-ethylphosphonic acid of melting point 228°–230° C. (decomposition); $[\alpha]_D^{20} = -31.5°$ (c=0.5% in acetic acid); $[\alpha]_{365}^{20} = -117°$ (c=0.5% in acetic acid).

(iv) In a manner analogous to that described in paragraph (ii) earlier, from 13.4 g (21 mmol) of the monobenzylamine salt of (1R)-1-[(N-benzyloxycarbonyl-L-alanyl-L-nitroarginyl)amino]-ethylphosphonic acid there were obtained, after treatment with propylene oxide, 11.3 g of crude product of melting point 200°–210° C. (decomposition). Recrystallisation from a mixture of water and ethanol gave 7.04 g of (1R)-1-(L-alanyl-L-nitroarginylamino)-ethylphosphonic acid of melting point 263°–265° C. (decomposition); $[\alpha]_D^{20} = -22.9°$ (c=0.5% in water); $[\alpha]_{365}^{20} = -71.9°$ (c=0.5% in water).

(B) The Process (i) In a manner analogous to that described in paragraph (A)(i)(b) of this Example, from 45 ml of the stock solution of N-benzyloxycarbonyl-sarcosine N-hydroxysuccinimide ester referred to in Example 1(A)(ii) and 5.96 g (15 mmol) of (1R)-1-(L-alanyl-L-nitroarginylamino)-ethylphosphonic acid there were obtained 11 g of crude monobenzylamine salt of (1R)-1-[(N-benzyloxycarbonyl-sarcosyl-L-alanyl-L-nitroarginyl)amino]-ethylphosphonic acid of melting point 230° C. (decomposition; softening from 195° C.). Recrystallisation of a sample of this monobenzylamine salt from a mixture of water, ethanol and diethyl ether gave the monobenzylamine salt of (1R)-1-[(N-benzyloxycarbonyl-sarcosyl-L-alanyl-L-nitroarginyl)amino]-ethylphosphonic acid of melting point 236°–239° C. (decomposition); $[\alpha]_D^{20} = -38.2°$ (c=0.5% in acetic acid); $[\alpha]_{365}^{20} = -141°$ (c=0.5% in acetic acid).

(ii) In a manner analogous to that described in paragraph (A)(ii) of this Example, from 10.5 g (15 mmol) of the monobenzylamine salt of (1R)-1-[(N-benzyloxycarbonyl-sarcosyl-L-alanyl-L-nitroarginyl)amino]-ethylphosphonic acid there were obtained 6.72 g of crude product of melting point 225°–235° C. (decomposition). Recrystallisation from a mixture of 50 ml of water (with filtration) and 150 ml of ethanol gave 5.25 g of (1R)-1-(n-sarcosyl-L-alanyl-L-nitroarginylamino)-ethylphosphonic acid of melting point 253°–255° C. (decomposition); $[\alpha]_D^{20} = -59.9°$ (c=0.55% in water); $[\alpha]_{365}^{20} = -195°$ (c=0.55% in water).

(iii) 3.92 g (8.4 mmol) of (1R)-1-(N-sarcosyl-L-alanyl-L-nitroarginylamino)-ethylphosphonic acid were dissolved in 120 ml of water and 0.8 g of 10% palladium-on-charcoal catalyst was added. The mixture was hydrogenated at room temperature and atmospheric pressure until the uptake of hydrogen ceased. The catalyst was filtered off and the solvent was removed by filtration. The gum-like residue was triturated with 150 ml of methanol and left to stand at room temperature. The separated solid was filtered off and washed with methanol and then with diethyl ether to give 3.05 g of crude product of melting point ca 200° C. (decomposition). Recrystallisation from a mixture of 40 ml of warm water (with filtration) and 140 ml of ethanol gave, as a flocculent crystalline precipitate, 2.44 g of (1R)-1-(N-sarcosyl-L-alanyl-L-arginylamino)-ethylphosphonic acid of melting point ca 205° C. (decomposition); $[\alpha]_D^{20} = -78.8°$ (c=0.5% in water); $[\alpha]_{365}^{20} = -293°$ (c=0.5% in water).

The following Example illustrates a typical pharmaceutical preparation provided by the present invention:

EXAMPLE 8

(A) The Preparation of the Starting Material (i) In a manner analogous to that described in Example 1(B)(i), from N-benzyloxycarbonyl-L-serine N-hydroxysuccinimide ester (prepared in situ as a gum from N-benzyloxycarbonyl-L-serine, N-hydroxysuccinimide and dicyclohexylcarbodiimide with dimethoxymethane as solvent) and (1R)-1-aminoethylphosphonic acid there was obtained the monobenzylamine salt of (1R)-1-[(N-benzyloxycarbonyl-L-seryl)amino]-ethylphosphonic acid of melting point 207°–210° C. (decomposition); $[\alpha]_D^{20} = -24.0°$ (c=0.5% in acetic acid).

(ii) In a manner analogous to that described in Example 3(ii), from the monobenzylamine salt of (1R)-1-[(N-benzyloxycarbonyl-L-seryl)amino]-ethylphosphonic acid there was obtained (1R)-1-(L-serylamino)-ethylphosphonic acid of melting point 250°–251° C. (decomposition); $[\alpha]_D^{20} = -41.7°$ (c=0.5% in water).

(iii) In a manner analogous to that described in Example 1(B)(i), from N-benzyloxycarbonyl-L-alanine and N-hydroxysuccinimide ester and (1R)-1-(L-serylamino)-ethylphosphonic acid there was obtained the monobenzylamine salt of (1R)-1-[(N-benzyloxycarbonyl-L-alanyl-L-seryl)amino]-ethylphosphonic acid of melting point 226°–228° C. (decomposition); $[\alpha]_D^{20} = -47.0°$ (c=0.5% in water).

(B) The Process (i) In a manner analogous to that described in Example 1(B)(i), from a stock solution of N-benzyloxycarbonyl-sarcosine N-hydroxysuccinimide ester and (1R)-1-(L-alanyl-L-serylamino)-ethylphosphonic acid there was obtained the monobenzylamine salt of (1R)-1-[(N-benzyloxycarbonyl-sarcosyl-L-alanyl-L-seryl)amino]-ethylphosphonic acid of melting point 219°–221° C. (decomposition); $[\alpha]_D^{20} = -60.5°$ (c=0.5% in water).

(iv) In a manner analogous to that described in Example 3(ii), from the monobenzylamine salt of (1R)-1-[(N-benzyloxycarbonyl-L-alanyl-L-seryl)amino]-ethylphosphonic acid there was obtained (1R)-1-(L-alanyl-L-serylamino)-ethylphosphonic acid of melting point 234°–235° C. (decomposition).

(ii) In a manner analogous to that described in Example 3(ii), from the monobenzylamine salt of (1R)-1-[(N-benzyloxycarbonyl-sarcosyl-L-alanyl-L-seryl)amino]-ethylphosphonic acid there was obtained (1R)-1-(N-sarcosyl-L-alanyl-L-serylamino)-ethylphosphonic acid of melting point 259°–260° C. (decomposition); $[\alpha]_D^{20} = -92.3°$ (c=0.5% in water).

EXAMPLE 9

(A) The Preparation of the Starting Material (i) In a manner analogous to that described in Example 1(B)(i), from N-benzyloxycarbonyl-L-alanine N-hydroxysuccinimide ester and (1R)-1-(L-norvalylamino)-ethylphosphonic acid there was obtained the monobenzylamine salt of (1R)-1-[(N-benzyloxycarbonyl-L-alanyl-L-norvalyl)amino]-ethylphosphonic acid of melting point 240°–243° C. (decomposition). A sample was recrystallised from hot water to give 0.11 g of product of melting point 234°–237° C. (decomposition); $[\alpha]_D^{20} = -39.1°$; $[\alpha]_{365}^{20} = -137°$ (c=0.49% in acetic acid).

(ii) In a manner analogous to that described in Example 5(A)(iii), from the monobenzylamine salt of (1R)-1-[(N-benzyloxycarbonyl-L-alanyl-L-norvalyl)amino]-ethylphosphonic acid there was obtained (1R)-1-(L-alanyl-L-norvalylamino)-ethylphosphonic acid of melting point 268°–270° C.; $[\alpha]_D^{20} = -50.4°$; $[\alpha]_{365}^{20} = -201°$ (c=0.46%, a freshly prepared solution in 1-N sodium hydroxide).

(B) The Process (i) In a manner analogous to that described in Example 1(B)(i), from a stock solution of N-benzyloxycarbonyl-sarcosine N-hydroxysuccinimide ester in dimethylformamide and (1R)-1-(L-alanyl-L-norvalylamino)-ethylphosphonic acid there was obtained the monobenzylamine salt of (1R)-1-[(N-benzyloxycarbonyl-sarcosyl-L-alanyl-L-norvalyl)amino]-ethylphosphonic acid of melting point 257°–259° C. (decomposition); $[\alpha]_D^{20} = -43.7°$; $[\alpha]_{365}^{20} = -164°$ (c=0.49% in acetic acid).

(ii) In a manner analogous to that described in Example 5(A)(iii), from the monobenzylamine salt of (1R)-1-[(N-benzyloxycarbonyl-sarcosyl-L-alanyl-L-norvalyl)amino]-ethylphosphonic acid there was obtained (1R)-1-(N-sarcosyl-L-alanyl-L-norvalylamino)-ethylphosphonic acid of melting point 291°–292° C. (decomposition); $[\alpha]_D^{20} = -110°$; $[\alpha]_{365}^{20} = -391°$ (c=0.26% in water).

EXAMPLE 10

(A) The Preparation of the Starting Material (i) In a manner analogous to that described in Example 1(B)(i), from N-benzyloxycarbonyl-L-serine N-hydroxysuccinimide ester [prepared in situ in a manner analogous to that described in Example 8(A)(i)] and (1R)-1-(L-alanylamino)-ethylphosphonic acid, there was obtained the monobenzylamine salt of (1R)-1-[(N-benzyloxycarbonyl-L-seryl-L-alanyl)amino]-ethylphosphonic acid of melting point 200°–205° C. (decomposition); $[\alpha]_D^{20} = -53.7°$; $[\alpha]_{365}^{20} = -189°$ (c=0.3% in water).

(ii) In a manner analogous to that described in Example 3(ii) from the monobenzylamine salt of (1R)-1-[(N-benzyloxycarbonyl-L-seryl-L-alanyl)amino]-ethylphosphonic acid there was obtained (1R)-1-(L-seryl-L-alanylamino)-ethylphosphonic acid of melting point 256°–257° C. (decomposition); $[\alpha]_D^{20} = -61.4°$; $[\alpha]_{365}^{20} = -222°$ (c=0.5% in water).

(B) The Process (i) In a manner analogous to that described in Example 1(B)(i), from a stock solution of N-benzyloxycarbonyl-sarcosine-N-hydroxysuccinimide ester and (1R)-1-

(L-seryl-L-alanylamino)-ethylphosphonic acid there was obtained the hygroscopic monobenzylamine salt of (1R)-1-[(N-benzyloxycarbonyl-sarcosyl-L-seryl-L-alanyl)amino]-ethylphosphonic acid of melting point 204°–205° C. (decomposition); $[\alpha]_D^{20} = -55.9°$; $[\alpha]_{365}^{20} = -201°$ (c=0.5% in water).

(ii) In a manner analogous to that described in Example 3(ii), from the monobenzylamine salt of (1R)-1-[(N-benzyloxycarbonyl-sarcosyl-L-seryl-L-alanyl)amino]-ethylphosphonic acid there was obtained (1R)-1-(N-sarcosyl-L-seryl-L-alanylamino)-ethylphosphonic acid of melting point 249°–250° C. (decomposition); $[\alpha]_D^{20} = -85.2°$; $[\alpha]_{365}^{20} = -301°$ (c=0.5% in water).

EXAMPLE 11

(A) The Preparation of the Starting Material (i) In a manner analogous to that described in Example 7(A)(i)(a), but using N-ethylmorpholine in place of triethylamine, from N-benzyloxycarbonyl-L-nitroarginine and (L-alanylamino)-ethylphosphonic acid there was obtained the monobenzylamine salt of (1R)-1-[(N-benzyloxycarbonyl-L-nitroarginyl-L-alanyl)amino]-ethylphosphonic acid of melting point 193°–203° (decomposition).

(ii) In a manner analogous to that described in Example 5 (A)(iii), from the monobenzylamine salt of (1R)-1-[(N-benzyloxycarbonyl-L-nitroarginyl-L-alanyl-)amino]-ethylphosphonic acid there was obtained (1R)-1-(L-nitroarginyl-L-alanylamino)-ethylphosphonic acid of melting point 224°–226° C. (decomposition): $[\alpha]_D^{20} = -26.0°$; $[\alpha]_{365}^{20} = -75.6°$ (c=0.43% in water).

(B) The Process (i) In a manner analogous to that described in Example 7(B)(i), from a stock solution of N-benzyloxycarbonyl-sarcosin-N-hydroxysuccinimide ester and (1R)-1-(L-nitroarginyl-L-alanylamino)-ethylphosphonic acid there was obtained the monobenzylamine salt of (1R)-1-[(N-benzyloxycarbonyl-sarcosyl-L-nitroarginyl-L-alanyl)amino]-ethylphosphonic acid of melting point 212°–215° C. (decomposition); Recrystallisation of a sample from water/ethanol/ether gave the product of melting point 219°–221° C. (decomposition); $[\alpha]_D^{20} = -35.6°$; $[\alpha]_{365}^{20} = -121°$ (c=0.55% in water).

(ii) In a manner analogous to that described in Example 7(A)(ii), from the monobenzylamine salt of (1R)-1-[(N-benzyloxycarbonyl-sarcosyl-L-nitroarginyl-L-alanyl)amino]-ethylphosphonic acid there was obtained (1R)-1-(N-sarcosyl-L-nitroarginyl-L-alanylamino)-ethylphosphonic acid of melting point 281°–283° C. (decomposition); $[\alpha]_D^{20} = -57.7°$; $[\alpha]_{365}^{20} = -193°$.

(iii) In a manner analogous to that described in Example 7(B)(iii), from (1R)-1-(N-sarcosyl-L-nitroarginyl-L-alanylamino)-ethylphosphonic acid there was obtained (1R)-1-(N-sarcosyl-L-arginyl-L-alanylamino)-ethylphosphonic acid of melting point ca 183° C. (decomposition); $[\alpha]_D^{20} = -59.8°$; $[\alpha]_{365}^{20} = -231°$ (c=0.51% in water).

EXAMPLE 12

(A) The Preparation of the Starting Material (i) In a manner analogous to that described in Example 9(A)(i), from N-benzyloxycarbonyl-L-norvaline N-hydroxysuccinimide ester and (1R)-1-(L-alanylamino)-ethylphosphonic acid there was obtained the monobenzylamine salt of (1R)-1-[(N-benzyloxycarbonyl-L-norvalyl-L-alanyl)amino]-ethylphosphonic acid of melting point 225°–229° C. (decomposition). Recrystallisation of a sample from hot water/ethanol/ether gave 0.35 g of product of melting point 230°–232° C. (decomposition); $[\alpha]_D^{20} = -40.3°$; $[\alpha]_{365}^{20} = -148°$ (c=0.51% in acetic acid).

(ii) In a manner analogous to that described in Example 5(A)(iii), from the monobenzylamine salt of (1R)-1-[(N-benzyloxycarbonyl-L-norvalyl-L-alanyl)amino]-ethyl-phosphonic acid there was obtained (1R)-1-(L-norvalyl-L-alanylamino)ethylphosphonic acid of melting point 260°–261° C. (decomposition); $[\alpha]_D^{20} = -46.5°$; $[\alpha]_{365}^{20} = -168°$ (c=0.51% in water).

(B) The Process (i) In a manner analogous to that described in Example 1(B)(i), from a stock solution of N-benzyloxycarbonyl-sarcosine N-hydroxysuccinimide ester and (1R)-1-(L-norvalyl-L-alanylamino)-ethylphosphonic acid there was obtained the monobenzylamine salt of (1R)-1-[(N-benzyloxycarbonyl-sarcosyl-L-norvalyl-L-alanyl)amino]-ethylphosphonic acid of melting point 233°–236° C. (decomposition); $[\alpha]_D^{20} = -41.8°$; $[\alpha]_{365}^{20} = -152°$ (c=0.49% in acetic acid).

(ii) In a manner analogous to that described in Example 5(A)(iii), from the monobenzylamine salt of (1R)-1-[(N-benzyloxycarbonyl-sarcosyl-L-norvalyl-L-alanyl)amino]-ethylphosphonic acid there was obtained (1R)-1-(N-sarcosyl-L-norvalyl-L-alanylamino)-ethylphosphonic acid of melting point 277°–279° C. (decomposition); $[\alpha]_D^{20} = -96.0°$; $[\alpha]_{365}^{20} = -348°$ (c=0.51% in water).

EXAMPLE 13

(A) The Preparation of the Starting Material (i) In a manner analogous to that described in Example 7(A)(i)(b), from N-benzyloxycarbonyl-L-nitroarginine and (1R)-1-(nitroarginylamino)-ethylphosphonic acid there was obtained the monobenzylamine salt of (1R)-1-[(N-benzyloxycarbonyl-L-nitroarginyl-L-nitroarginyl)amino]-ethylphosphonic acid of melting point ca 120° C. (decomposition). This material was used in the next step without further purification.

(ii) In a manner analogous to that described in Example 5(A)(iii), from the monobenzylamine salt of (1R)-1-[(N-benzyloxycarbonyl-L-nitroarginyl-L-nitroarginyl-)amino]-ethylphosphonic acid there was obtained (1R)-1-(L-nitroarginyl-L-nitroarginylamino)-ethylphosphonic acid of melting point ca 195° C. (decomposition). Recrystallisation of a sample from water/ethanol gave 0.29 g of product of melting point ca 203° C. (decomposition; $[\alpha]_D^{20} = -5.3°$; $[\alpha]_{365}^{20} = -9.7°$, (c=0.51% in water).

(B) The Process (i) In a manner analogous to that described in Example 7(B) (i), from a stock solution of N-benzyloxycarbonyl-sarcosine N-hydroxysuccinimide ester and (1R)-1-(L-nitroarginyl-L-nitroarginylamino)-ethylphosphonic acid there was obtained, after triturating the residue obtained by evaporating the acid eluate first with ether and then with acetone, (1R)-1-[(benzyloxycarbonyl-sarcosyl-L-nitroarginyl-L-nitroarginyl)amino]-ethylphosphonic acid of melting point 185°–189° (decomposition).

(ii) In a manner analogous to that described in Example 7(A) (ii), from (1R)-1-[(N-benzyloxycarbonyl-sarcosyl-L-nitroarginyl L-nitroarginyl)amino]-ethylphosphonic acid there was obtained (1R)-1-(N-sarcosyl-L-nitroarginyl-L-nitroarginylamino)-ethylphosphonic acid of melting point 228°–230° C. (decomposition); $[\alpha]_D^{20} = -34.3°$; $[\alpha]_{365}^{20} = -117°$ (c=0.51%, freshly prepared in 0.1-N sodium hydroxide).

(iii) In a manner analogous to that described in Example 7(B) (iii), from (1R)-1-(N-sarcosyl-L-nitroarginyl-L-nitroarginylamino)-ethylphosphonic acid there was obtained (1R)-1-(N-sarcosyl-L-arginyl-L-arginylamino)-ethylphosphonic acid of melting point ca 220° C. (decomposition;) $[\alpha]_D^{20} = -42.4°$; $[\alpha]_{365}^{20} = -160°$ (c=0.43% in water).

EXAMPLE 14

(A) The Preparation of the Starting Material (i) In a manner analogous to that described in Example 7(A)(i)(b), from N-benzyloxycarbonyl-L-norvaline N-hydroxysuccinimide ester and (1R)-1-(L-nitroarginylamino)-ethylphosphonic acid there was obtained, after evaporation of the acid eluate and trituration of the residue first with ether and then with acetone, (1R)-1-[(N-benzyloxycarbonyl-L-norvalyl-L-nitroarginyl-)amino]-ethylphosphonic acid of melting point 202°–205° C. (decomposition).

(ii) In a manner analogous to that described in Example 7(A)(ii), from (1R)-1-[(N-benzyloxycarbonyl-L-norvalyl-L-nitroarginyl)amino]-ethylphosphonic acid there was obtained (1R)-1-(L-norvalyl-L-nitroarginylamino)-ethylphosphonic acid of melting point 267°–269° C. (decomposition); $[\alpha]_D^{20} = -23.0°$; $[\alpha]_{365}^{20} = -84.0°$ (c=0.57%, freshly prepared in 0.1-N sodium hydroxide).

(B) The Process (i) In a manner analogous to that described in Example 7(B)(i), from a stock solution of N-benzyloxycarbonyl-sarcosine N-hydroxysuccinimide ester and (1R)-1-(L-norvalyl-L-nitroarginylamino)-ethylphosphonic acid there was obtained the monobenzylamine salt of (1R)-1-[(N-benzyloxycarbonyl-sarcosyl-L-norvalyl-L-nitroarginyl)amino]-ethylphosphonic acid of melting point 230°–235° C. (decomposition).

(ii) In a manner analogous to that described in Example 7(A)(ii), from the monobenzylamine salt of (1R)-1-[(N-benzyloxycarbonyl-sarcosyl-L-norvalyl-L-nitroarginyl)amino]-ethylphosphonic acid there was obtained (1R)-1-(N-sarcosyl-L-norvalyl-L-nitroarginylamino)-ethylphosphonic acid of melting point 246°–249° C. (decomposition); $[\alpha]_D^{20} = -47.4°$; $[\alpha]_{365}^{20} = -157°$ (c=53% in water).

(iii) In a manner analogous to that described in Example 7(B)(iii), from (1R)-1-(N-sarcosyl-L-norvalyl-L-nitroarginylamino)-ethylphosphonic acid there was obtained (1R)-1-(N-sarcosyl-L-norvalyl-L-arginylamino)-ethylphosphonic acid of melting point ca 200° C.; $[\alpha]_D^{20} = -68.1°$; $[\alpha]_{365}^{20} = -251°$ (c=0.52% in water).

EXAMPLE 15

(A) The Preparation of the Starting Material (i) In a manner analogous to that described in Example 1(B)(i), from N-benzyloxycarbonyl-L-norvaline N-hydroxysuccinimide ester and (1R)-1-(L-norvalylamino)-ethylphosphonic acid there was obtained the monobenzylamine salt of (1R)-1-[(N-benzyloxycarbonyl-L-norvalyl-L-norvalyl)amino]-ethylphosphonic acid of melting point 243°–245° C. (decomposition). A sample was recrystallised from hot water to give the pure monobenzylamine salt of melting point 247°–249° C. (decomposition); $[\alpha]_D^{20} = -35.7°$; $[\alpha]_{365}^{20} = -125°$ (c=0.46% in acetic acid).

(ii) In a manner analogous to that described in Example 5(A)(iii), from the monobenzylamine salt of (1R)-1-[(N-benzyloxycarbonyl-L-norvalyl-L-norvalyl)amino]-ethylphosphonic acid there was obtained (1R)-1-(L-norvalyl-L-norvalylamino)-ethylphosphonic acid of melting point 273°–275° C. (decomposition); $[\alpha]_D^{20} = -36.0°$; $[\alpha]_{365}^{20} = -153°$, (c=0.5% freshly prepared in 0.1-N sodium hydroxide).

(B) The Process (i) In a manner analogous to that described in Example 1(B)(i), from a stock solution of N-benzyloxycarbonyl-sarcosine N-hydroxysuccinimide ester and (1R)-1-(L-norvalyl-L-norvalylamino)-ethylphosphonic acid there was obtained, on evaporation, the crude coupled product. This product was too insoluble in aqueous methanol for the usual ion-exchange procedure and was therefore treated with water and 2-N hydrochloric acid. The mixture was stirred at room temperature and the precipitate was filtered off to give crude product of melting point 210°–214° C. (decomposition). Stirring with acetone then gave (1R)-1-[(N-benzyloxycarbonyl-sarcosyl-L-norvalyl-L-norvalyl)amino]-ethylphosphonic acid of melting point 217°–219° C. (decomposition); $[\alpha]_D^{20} = -30.2°$; $[\alpha]_{365}^{20} = -113°$ (c=0.48% in dimethyl sulphoxide).

(ii) In a manner analogous to that described in Example 5(A)(iii), from (1R)-1-[(N-benzyloxycarbonyl-sarcosyl-L-norvalyl-L-norvalyl)amino]-ethylphosphonic acid there was obtained (1R)-1-(N-sarcosyl-L-norvalyl-L-norvalylamino)-ethylphosphonic acid of melting point 275°–277° C. (decomposition); $[\alpha]_D^{20} = -83.5°$; $[\alpha]_{365}^{20} = -306°$ (c=0.3% in water).

EXAMPLE 16

(A) The Preparation of the Starting Material (i) In a manner analogous to that described in Example 1(B)(i), from N-benzyloxycarbonyl-glycine N-hydroxysuccinimide ester and (1R)-1-(L-norvalylamino)-ethylphosphonic acid there was obtained the monobenzylamine salt of (1R)-1-[(N-benzyloxycarbonyl)-glycyl-L-norvalyl)amino]-ethylphosphonic acid of melting point 217°–220° C. (decomposition).

(ii) In a manner analogous to that described in Example 5(A)(iii), from the monobenzylamine salt of (1R)-1-[(N-benzyloxycarbonyl-glycyl-L-norvalyl)amino]-ethylphosphonic acid there was obtained (1R)-1-(glycyl-L-norvalylamino)-ethylphosphonic acid of melting point 265°–267° C. (decomposition); $[\alpha]_D^{20} = -74.2°$; $[\alpha]_{365}^{20} = -271°$ (c=0.49% in water).

(B) The Process (i) In a manner analogous to that described in Example 1(B)(i), from a stock solution of N-benzyloxycarbonyl-sarcosine N-hydroxysuccinimide ester and (1R)-1-(glycyl-L-norvalylamino)-ethylphosphonic acid there was obtained the monobenzylamine salt of (1R)-1-[(N-benzyloxycarbonyl-sarcosyl-glycyl-L-norvalyl)amino]-ethylphosphonic acid of melting point 225°–230° C. (decomposition).

(ii) In a manner analogous to that described in Example 5(A)(iii), from the monobenzylamine salt of (1R)-1-[(N-benzyloxycarbonyl-sarcosyl-glycyl-L-norvalyl- )amino]-ethylphosphonic acid there was obtained (1R)-1-(N-sarcosyl-glycyl-L-norvalylamino)-ethylphosphonic acid of melting point 255°–257° C. (decomposition); $[\alpha]_D^{20} = -64.2°$; $[\alpha]_{365}^{20} = -235°$ (c=0.49% in water).

EXAMPLE 17

(A) The Preparation of the Starting Material (i) In a manner analogous to that described in Example 7(A)(i)(b), from N-benzyloxycarbonyl-L-nitroarginine and (1R)-1-[L-norvalylamino]-ethylphosphonic acid there was obtained the monobenzylamine salt of (1R)-1-[(N-benzyloxycarbonyl-L-nitroarginyl-L-norvalyl)amino]-ethylphosphonic acid of melting point 191°–196° C. (decomposition) which was used directly in the next step.

(ii) In a manner analogous to that described in Example 7(A)(ii), from the monobenzylamine salt of (1R)-1-[(N-benzyloxycarbonyl-L-nitroarginyl-L-norvalyl)amino]-ethylphosphonic acid there was obtained (1R)-1-(L-nitroarginyl-L-norvalylamino)-ethylphosphonic acid of melting point 240°–242° C. (decomposition); $[\alpha]_D^{20} = -14.0°$; $[\alpha]_{365}^{20} = -46.7°$ (c=0.49% in water).

(B) The Process (i) In a manner analogous to that described in Example 7(B)(i), from a stock solution of N-benzyloxycarbonyl-sarcosine N-hydroxysuccinimide ester and (1R)-1-(L-nitroarginyl-L-norvalylamino)-ethylphosphonic acid there was obtained the monobenzylamine salt of (1R)-1-[(N-benzyloxycarbonyl-sarcosyl-L-nitroarginyl-L-norvalyl)amino]-ethylphosphonic acid of melting point 208°–212° C. (decomposition), which was used in the next step.

(ii) In a manner analogous to that described in Example 7(A)(ii), from the monobenzylamine salt of (1R)-1-[(N-benzyloxycarbonyl-sarcosyl-L-nitroarginyl-L-norvalyl)amino]-ethylphosphonic acid there was obtained (1R)-1-(N-sarcosyl-L-nitroarginyl-L-norvalylamino)-ethylphosphonic acid of melting point 245°–250° C.; $[\alpha]_D^{20} = -51.4°$; $[\alpha]_{365}^{20} = -179°$ (c=0.49% freshly prepared in 0.1-N sodium hydroxide).

(iii) In a manner analogous to that described in Example 7(B)(iii), from (1R)-1-(N-sarcosyl-L-nitroarginyl-L-norvalylamino)-ethylphosphonic acid there was obtained (1R)-1-(N-sarcosyl-L-arginyl-L-norvalylamino)-ethylphosphonic acid of melting point ca 220° C. (decomposition); $[\alpha]_D^{20} = -56.9°$; $[\alpha]_{365}^{20} = -223°$ (c=0.51% in water).

EXAMPLE 18

(A) The Preparation of the Starting Material (i)(a) In a manner analogous to that described in Example 7(A)(i)(a), from N-benzyloxycarbonyl-L-valine and (1R)-1-[L-norvalylamino]-ethylphosphonic acid there was obtained (1R)-1-[(N-benzyloxycarbonyl-L-valyl-L-norvalyl)amino]-ethylphosphonic acid together with (1R)-1-[(N-isobutoxycarbonyl-L-norvalyl)amino]-ethylphosphonic acid according to the nmr spectrum. This material was used in the next step without further purification.

(i)(b) In a manner analogous to that described in Example 1(B)(i), from (1R)-1-(L-norvalylamino)-ethylphosphonic acid and N-benzyloxycarbonyl-L-valine N-hydroxysuccinimide ester there was obtained, after evaporation of the solvents, a residue which did not dissolve in water. The aqueous suspension was stirred 2-N hydrochloric acid was added to a pH below 1 to give a gelatinous precipitate which was left to stand at 0° C. overnight. The precipitate was filtered off and dried to give a waxy solid. This solid was stirred with acetone and filtered to give crude (1R)-1-[N-benzyloxycarbonyl-L-valyl-L-norvalyl)amino]-ethylphosphonic acid of melting point 205°–210° C. (decomposition).

(ii)(a) In a manner analogous to that described in Example 7(A)(ii), from crude (1R)-1-[(N-benzyloxycarbonyl-L-valyl-L-norvalyl)amino]-ethylphosphonic acid [prepared as described in part (A)(i)(a) of this Example] there was obtained (1R)-1-(L-valyl-L-norvalylamino)-ethylphosphonic acid of melting point 268°–270° C. (decomposition); $[\alpha]_D^{20} = -33.4°$; $[\alpha]_{365}^{20} = -110°$ (c=0.47% in 1-N hydrochloric acid).

(ii)(b) In a manner analogous to that described in Example 7(A)(ii), from crude (1R)-1-[(N-benzyloxycarbonyl-L-valyl-L-norvalyl)amino]-ethylphosphonic acid [prepared as described in part (A)(i)(b) of this Example] there was obtained (1R)-1-(L-valyl-L-norvalylamino)-ethylphosphonic acid of melting point 268°–270° C. (decomposition); $[\alpha]_D^{20} = -34.6°$; $[\alpha]_{365}^{20} = -114°$ (c=0.54% in 1-N hydrochloric acid).

(B) The Process (i) In a manner analogous to that described in Example 1(B)(i), from (1R)-1-(L-valyl-L-norvalylamino)ethylphosphonic acid and a stock solution of N-benzyloxycarbonyl-sarcosine N-hydroxysuccinimide ester there was obtained (1R)-1-[(N-benzyloxycarbonyl-sarcosyl-L-valyl-L-norvalyl)amino]-ethyl-phosphonic acid of melting point 228°–230° C. (decomposition).

(ii) In a manner analogous to that described in Example 5(A)(iii), from (1R)-1-[(N-benzyloxycarbonyl-sarcosyl-L-valyl-L-norvalyl)amino]-ethylphosphonic acid there was obtained (1R)-1-(N-sarcosyl-L-valyl-L-norvalylamino)-ethylphosphonic acid of melting point 280°–282° C. (decomposition); $[\alpha]_D^{20} = -90.4°$: $[\alpha]_{365}^{20} = -329°$ (c=0.52% in water).

EXAMPLE 19

(A) The Preparation of the Starting Material (i) In a manner analogous to that described in J. Org. Chem. 35, page 1914 (1970), 10.45 g (50 mmol) of N-benzyloxycarbonyl-glycine was stirred in 100 ml of dry dimethylformamide at room temperature and treated with 62.4 g (400 mmol) of ethyl iodide and ca 46 g (180 mmol) of silver oxide.

The mixture was stirred overnight and filtered, the filtrate was diluted with 400 ml of methylene chloride and refrigerated overnight. The precipitated silver iodide was filtered off and the filtrate was washed twice with 100 ml portions of aqueous potassium cyanide solution and then three times with 150 ml portions of water. The organic layer was dried over sodium sulphate, filtered and evaporated, first at the water pump and then at the oil pump, to give 14.25 g of crude ethyl N-benzyloxycarbonyl-N-ethyl glycinate in the form of a yellow oil.

(ii) In a manner analogous to that described in the aforementioned literature reference, 14.25 g (ca 50 mmol) of crude ethyl N-benzyloxycarbonyl-N-ethyl glycinate were stirred at room temperature with 150 ml of ethanol and treated with 50 ml of 1-N aqueous sodium hydroxide. The mixture was stirred for a further 30 minutes. Solvents were evaporated off and the residual oil was dissolved in 150 ml of water, cooled to 0° C.

and treated with ca 30 ml of 2-N HCl to pH 2 (Congo red). The resulting oily precipitate was extracted with two 200 ml portions of ethyl acetate, with back-washing of the organic phases with two 200 ml portions of water. The combined ethyl acetate extracts were dried over sodium sulphate, filtered and evaporated to give an oil. Trituration with carbon tetrachloride gave a solid which was filtered off. The filtrate was evaporated to give ca 9.5 g N-benzyloxycarbonyl-N-ethyl-glycine in the form of an oil which had a satisfactory nmr spectrum. This product was used in the next step without further purification.

(iii) In a manner analogous to that described in Example 1 (A)(ii), from N-benzyloxycarbonyl-N-ethyl-glycine there was obtained N-benzyloxycarbonyl-N-ethyl glycine N-hydroxysuccinimide ester in the form of an oil which was dissolved in dimethylformamide and used in the next step without further purification.

(B) The Process (i) In a manner analogous to that described in Example 1(B)(i), from the aforementioned solution of N-benzyloxycarbonyl-N-ethyl-glycine N-hydroxysuccinimide ester and (1R)-1-(L-alanyl-L-alanylamino)-ethylphosphonic acid there was obtained an acid eluate from the resin. This eluate was evaporated to give a gum which was partitioned between water and methylene chloride. A substantial amount of insoluble solid was then obtained which was filtered off and dried to give crude product of melting point 186°–189° C. (decomposition). Recrystallisation from ethanol gave (1R)-1-[(N-benzyloxycarbonyl-N-ethyl-glycyl-L-alanyl-L-alanyl)amino]-ethylphosphonic acid of melting point 180°–181° C. (decomposition); $[\alpha]_D^{20} = -24.5°$; $[\alpha]_{365}^{20} = -101°$ (c=0.5% in dimethylformamide).

The foregoing methylene chloride/water filtrate was separated into organic and aqueous layers and the aqueous layer was back-washed with 250 ml of methylene chloride. The aqueous layer was then titrated with benzylamine to pH 4.5 to give the monobenzylamine salt of (1R)-1-[(N-benzyloxycarbonyl-N-ethyl-glycyl-L-alanyl-L-alanyl)amino]-ethylphosphonic acid of melting point 219°–223° C. (decomposition; $[\alpha]_D^{20} = -67.6°$: $[\alpha]_{365}^{20} = -236°$ (c=0.5% in water).

(ii) (1R)-1-[(N-benzyloxycarbonyl-N-ethyl-glycyl-L-alanyl)amino]-ethylphosphonic acid was dissolved in water and 10% palladium-on-charcoal catalyst, methanol and a few drops of acetic acid were added. The mixture was hydrogenated at room temperature and 50 atm. pressure overnight. The catalyst was filtered off and the filtrate was evaporated and re-evaporated with two portions of n-propanol. The residual solid was recrystallised from water/ethanol to give (1R)-1-(N-ethyl-glycyl-L-alanyl-L-alanylamino)-ethyl-phosphonic acid of melting point 267°–270° C. (decomposition); $[\alpha]_D^{20} = 1421°$ (c=0.5% in water).

EXAMPLE 20

(A) The Preparation of the Starting Material (i) In a manner analogous to that described in Example 19(A)(i), from N-benzyloxycarbonyl-glycine, allyl iodide and silver oxide in dry dimethylformamide there was obtained crude allyl N-allyl-N-benzyloxycarbonyl-glycinate in the form of a yellow oil.

(ii) In a manner analogous to that described in Example 19(A)(ii), from allyl-N-allyl-N-benzyloxycarbonyl-glycinate there was obtained N-allyl-N-benzyloxycarbonyl-glycine in the form of an oil.

(iii) In a manner analogous to that described in Example 1(A)(ii), from N-allyl-N-benzyloxycarbonyl-glycine there was obtained N-allyl-N-benzyloxycarbonyl-glycine N-hydroxysuccinimide ester in the form of a yellow oil which was dissolved in 25 ml of dimethylformamide and used in the next step without further purification.

(B) The Process (i) In a manner analogous to that described in Example 1(B)(i), from the aforementioned solution of N-allyl-N-benzyloxycarbonyl-glycine N-hydroxysuccinimide ester and (1R)-1-(L-alanyl-L-alanylamino)ethylphosphonic acid there was obtained, from the water/methylene chloride partition of the gum from the acid eluate, a solid which, according to thin-layer chromatography, appeared to be pure (1R)-1-[(N-allyl-N-benzyloxycarbonyl-glycyl-L-alanyl-L-alanyl)amino]-ethylphosphonic acid.

The aforementioned water/methylene chloride filtrate was separated into the layers. The aqueous layer was washed with methylene chloride and then evaporated to give a gum which was dissolved in ethanol/water and converted into the benzylamine salt. Evaporation gave a gummy solid which was recrystallised from 90% ethanol/ether to give the monobenzylamine salt of (1R)-1-[(N-allyl-N-benzyloxycarbonyl-glycyl-L-alanyl-L-alanyl)amino]-ethylphosphonic acid of melting point 233°–235° C. (decomposition); $[\alpha]_D^{20} = -45.1°$; $[\alpha]_{365}^{20} = -170°$ (c=0.5% in acetic acid).

(ii) In a manner analogous to that described in Example 1(B)(ii), from the monobenzylamine salt of (1R)-1-[(N-allyl-N-benzyloxycarbonyl-glycyl-L-alanyl-L-alanyl)amino]-ethylphosphonic acid, but using water/ethanol (1:1) for the ion-exchange step to generate the free acid, there was obtained, after hydrogenolysis of the N-benzyloxycarbonyl group in the usual way but with concomitant reduction of the allyl group to the n-propyl group, the crude product in the form of a gel. Crystallisation from water/ethanol gave (1R)-1-[N-(n-propyl)-glycyl-L-alanyl-L-alanylamino]-ethylphosphonic acid of melting point 263°–264° C. (decomposition); $[\alpha]_D^{20} = -110°$; $[\alpha]_{365}^{20} = -392°$ (c=1% in water).

EXAMPLE 21

In a manner analogous to that described in Example 7 (A)(ii), from the monobenzylamine salt of (1R)-1-[(N-allyl-N-benzyloxycarbonyl-glycyl-L-alanyl-L-alanyl)amino]-ethylphosphonic acid [prepared as described in Example 20(B)(i)] there was obtained (1R)-1-(N-allyl-glycyl-L-alanyl-L-alanylamino)-ethylphosphonic acid of melting point 251°–253° C. (decomposition); $[\alpha]_D^{20} = -110°$; $[\alpha]_{365}^{20} = -394°$ (c=1% in water).

EXAMPLE 22

(A) The Preparation of the Starting Material (i) In a manner analogous to that described in Example 19(A)(i), from N-benzyloxycarbonyl-glycine, n-hexyl iodide and silver oxide in dry dimethylformamide there was obtained crude n-hexyl N-benzyloxycarbonyl-N-(n-hexyl)-glycinate in the form of an oil.

(ii) In a manner analogous to that described in Example 19(A)(ii) from n-hexyl N-benzyloxycarbonyl-N-(n- hexyl)-glycinate there was obtained N-benzyloxycarbonyl-N-(n-hexyl)-glycine in the form of an oil.

(iii) In a manner analogous to that described in Example 1(A)(ii), from N-benzyloxycarbonyl-N-(n-hexyl)-glycine there was obtained N-benzyloxycarbonyl-N-(n-hexyl)-glycine N-hydroxysuccinimide ester in the form of a yellow oil which was dissolved in dimethylformamide and used in the next step without further purification.

(B) The Process (i) In a manner analogous to that described in Example 1(B)(i), from the aforementioned solution of N-benzyloxycarbonyl-N-(n-hexyl)-glycine N-hydroxysuccinimide ester and (1R)-1-(L-alanyl-L-alanylamino)-ethylphosphonic acid there was obtained an acid eluate after the treatment with ion exchange resin. The eluate was evaporated to give a solid which was partitioned between water and ethyl acetate. The layers were separated, the aqueous phase was washed with ethyl acetate and the organic phases were back-washed separately with water. The combined ethyl acetate extracts were dried over sodium sulphate and evaporated to give a yellow solid which was triturated with ether and filtered to give a hygroscopic crude product of melting point 183°–185° C. (decomposition). Recrystallisation from ethyl acetate/ether gave (1R)-1-[(N-benzyloxycarbonyl-N-(n-hexyl)-glycyl-L-alanyl-L-alanyl-)amino]-ethylphosphonic acid of melting point 177°–179° C. (decomposition); $[\alpha]_D^{20} = -46.1°$; $[\alpha]_{365}^{20} = -173°$ (c=0.5% in acetic acid).

(ii) In a manner analogous to that described in Example 5(A)(iii), from (1R)-1-[(N-benzyloxycarbonyl-N-(n-hexyl)-glycyl-L-alanyl-L-alanyl)amino]-ethylphosphonic acid there was obtained (1R)-1-(N-(n-hexyl)-glycyl-L-alanyl-L-alanylamino)-ethylphosphonic acid of melting point 262°–265° C. (decomposition); $[\alpha]_D^{20} = -88.2°$; $[\alpha]_{365}^{20} = -323°$ (c=0.5% in fresh 0.1-N sodium hydroxide).

EXAMPLE 23

(A) The Preparation of the Starting Material (i) In a manner analogous to that described in Example 1(A)(ii), from N-benzyloxycarbonyl-N-methyl-L-alanine [prepared as described in J. Org. Chem 35, p. 1915 (1970)] there was obtained N-benzyloxycarbonyl-N-methyl-L-alanine N-hydroxysuccinimide ester in the form of an oil.

(B) The Process (i) In a manner analogous to that described in Example 1(B)(i), from N-benzyloxycarbonyl-N-methyl-L-alanine N-hydroxysuccinimide ester in dimethylformamide and (1R)-1-(L-alanyl-L-alanylamino)-ethylphosphonic acid there was obtained an acid eluate from the cation exchange resin. Evaporation of this eluate gave a solid which was triturated with water and filtered off. The solid was triturated on the filter with acetone and recrystallised from ethanol to give (1R)-1-[(N-benzyloxycarbonyl-N-methyl-L-alanyl-L-alanyl-L-alanyl-)amino]-ethylphosphonic acid of melting point 225°–226° C. (decomposition); $[\alpha]_D^{20} = -99.3°$; $[\alpha]_{365}^{20} = -348°$ (c=0.5% in water).

(ii) In a manner analogous to that described in Example 19(B)(ii), from (1R)-1-[(N-benzyloxycarbonyl-N-methyl-L-alanyl-L-alanyl-L-alanyl)amino]-ethylphosphonic acid, but carrying out the hydrogenation in aqueous ethanol instead of aqueous methanol, there was obtained (1R)-1-(N-methyl-L-alanyl-L-alanyl-L-alanylamino)-ethylphosphonic acid of melting point 318°–320° C. (decomposition); $[\alpha]_D^{20} = -121°$; $[\alpha]_{365}^{20} = -418°$ (c=0.5% in water).

EXAMPLE 24

(A) The Preparation of the Starting Material (i) In a manner analogous to that described in Example 19 (A)(i), from N-benzyloxycarbonyl-L-norvaline, methyl iodide and silver oxide in dry dimethylformamide there was obtained in the form of a yellow oil, crude methyl N-benzyloxycarbonyl-N-methyl-L-norvalinate.

(ii) In a manner analogous to that described in Example 19(A)(ii), from methyl N-benzyloxycarbonyl-N-methyl-L-norvalinate there was obtained N-benzyloxycarbonyl-N-methyl-L-norvaline in the form of an oil.

(iii) In a manner analogous to that described in Example 1(A)(ii), from N-benzyloxycarbonyl-N-methyl-L-norvaline there was obtained N-benzyloxycarbonyl-N-methyl-L-norvaline N-hydroxysuccinimide ester in the form of an oil which was dissolved in dimethylformamide and used in the next step.

(B) The Process (i) In a manner analogous to that described in Example 1(B)(i), from the solution prepared in part (A)(iii) of this Example and (1R)-1-(L-norvalyl-L-norvalylamino)-ethylphosphonic acid [prepared as described in Example 15(A)(ii)] there was obtained (1R)-1-[(N-benzyloxycarbonyl-N-methyl-L-norvalyl-L-norvalyl-L-norvalyl)amino]-ethylphosphonic acid of melting point 195°–200° C. (decomposition; $[\alpha]_D^{20} = -28.7°$; $[\alpha]_{365}^{20} = -116°$ (c=0.5% in dimethylformamide).

(ii) In a manner analogous to that described in Example 5(A)(iii), from (1R)-1-[(N-benzyloxycarbonyl-N-methyl-L-norvalyl-L-norvalyl-L-norvalyl)amino]-ethylphosphonic acid there was obtained (1R)-1-(N-methyl-L-norvalyl-L-norvalyl-L-norvalylamino)-ethylphosphonic acid of melting point 307°–309° C. (decomposition); $[\alpha]_D^{20} = -81.1°$; $[\alpha]_{365}^{20} = -291°$ (c=0.5%, freshly prepared in 0.1-N sodium hydroxide).

EXAMPLE 25

(A) The Preparation of the Starting Material (i) In a manner analogous to that described in Example 19 (A)(i), from N-benzyloxycarbonyl-L-valine, methyl iodide and silver oxide in dry dimethylformamide there was obtained methyl N-benzyloxycarbonyl-N-methyl-L-valinate in the form of an oil.

(ii) In a manner analogous to that described in Example 19(A)(ii), from methyl N-benzyloxycarbonyl-N-methyl-L-valinate there was obtained crude N-benzyloxycarbonyl-N-methyl-L-valine which was used in the next step without further purification. The pure compound has a melting point of 64°–65° C.; $[\alpha]_{365}^{20} = -318°$ (c=0.98% in ethanol).

(iii) In a manner analogous to that described in Example 1(A)(ii), from crude N-benzyloxycarbonyl-N-methyl-L-valine there was obtained N-benzyloxycarbonyl-N-methyl-L-valine N-hydroxysuccinimide ester in the form of an oil which was taken up in dimethylformamide and used in the next step.

(B) The Process (i) In a manner analogous to that described in Example 1(B)(i), from the aforementioned solution of N-benzyloxycarbonyl-N-methyl-L-valine N-hydroxysuccinimide ester and (1R)-1-(L-valyl-L-norvalylamino)-ethylphosphonic acid (prepared as described in Example 18) there was obtained, after evaporation and treatment with 0.2-N hydrochloric acid, a gum. This gum was treated with methylene chloride to give an emulsion to which methanol was added. Two layers formed. The lower layer was evaporated and the gum obtained was triturated with ether, then with water and finally with aceton to give (1R)-1-[(N-benzyloxycarbonyl-N-methyl-L-valyl-L-valyl-N-norvalyl)amino]-ethylphosphonic acid of melting point 194°–197° C. (decomposition).

(ii) In a manner analogous to that described in Example 5(A)(iii), from (1R)-1[(N-benzyloxycarbonyl-N-methyl-L-valyl-L-valyl-L-norvalyl)amino]-ethylphosphonic acid there was obtained (1R)-1-(N-methyl-L-valyl-L-valyl-L-norvalyl)amino]-ethylphosphonic acid of melting point 309°–312° C. (decomposition); $[\alpha]_D^{20} = -55.1°$; $[\alpha]_{365}^{20} = -215°$ (c=0.56% in trifluoroacetic acid).

EXAMPLE 26

(A) The Preparation of the Starting Material (i) In a manner analogous to that described in Example 19(A)(i), from N-benzyloxycarbonyl-L-leucine, methyl iodide and silver oxide in dry dimethylformamide there was obtained methyl N-benzyloxycarbonyl-N-methyl-L-leucinate in the form of an oil.

(ii) In a manner analogous to that described in Example 19(A)(ii) from methyl N-benzyloxycarbonyl-N-methyl-L-leucinate there was obtained an oil which solidified on standing. Trituration with petroleum ether and filtration gave N-benzyloxycarbonyl-N-methyl-L-leucine of melting point 69°–71° C.; $[\alpha]_D^{20} = -22.0°$; $[\alpha]_{365}^{20} = -91.2°$ (c=0.5% in ethyl acetate).

(iii) In a manner analogous to that described in Example 1(A)(ii), from N-benzyloxycarbonyl-N-methyl-L-leucine there was obtained the crude product in the form of an oil. Trituration with petroleum ether gave N-benzyloxycarbonyl-N-methyl-L-leucine N-hydroxysuccinimide ester in the form of a solid of melting point 73°–75° C.; $[\alpha]_D^{20} = -46.9°$; $[\alpha]_{365}^{20} = -178°$ (c=0.5% in ethyl acetate).

(B) The Process (i) 3.23 g (10 mmol) of (1R)-1-(L-norvalyl-L-norvalylamino)-ethylphosphonic acid (prepared as described in Example 15) was stirred at 0° C. with 30 ml of water, 2.8 ml (20 mmol) of triethylamine and 60 ml of dimethylformamide. To the slurry were added 4.7 g (12.5 mmol) of N-benzyloxycarbonyl-N-methyl-L-leucine N-hydroxysuccinimide ester. The mixture was stirred for a further 2 hours at 0° C. then for 16 hours at room temperature to give a heterogeneous mixture. A solid was filtered off and the filtrate was evaporated at the oil pump to give ca 6 g of an oil which was stirred with 100 ml of water and 10 ml of 2-N hydrochloric acid were added. The mixture was stirred for 2 hours at room temperature and then 100 ml of methylene chloride were added. The layers were separated and the aqueous phase was extracted with 100 ml of methylene chloride and then with 50 ml of methylene chloride. The organic extracts were back-washed separately with two 50 ml portions of water, dried and evaporated to give ca 4.7 g of an oil which was treated with benzylamine. Evaporation and trituration with acetone gave 1.10 g of the monobenzylamine salt of (1R)-1-[(N-benzyloxycarbonyl-N-methyl-L-leucyl-L-norvalyl-L-norvalyl)amino]-ethylphosphonic acid of melting point 215°–218° C. (decomposition).

(ii) In a manner analogous to that described in Example 7(A)(ii), from (1R)-1-[(N-benzyloxycarbonyl-N-methyl-L-leucyl-L-norvalyl-L-norvalyl)amino]-ethylphosphonic acid there was obtained (1R)-1-[(N-methyl-L-leucyl-L-norvalyl-L-norvalyl) amino]-ethylphosphonic acid of melting point 317° C.–318° C. (decomposition); $[\alpha]_D^{20} = -39.9°$: $[\alpha]_{365}^{20} = -159°$ (c=0.5% in trifluoroacetic acid).

EXAMPLE 27

(i) In a manner analogous to that described in Example 1(B)(i), from a stock solution of N-benzyloxycarbonyl-sarcosine N-hydroxysuccinimide and (1R)-1-(L-alanylamino)-ethylphosphonic acid there was obtained the monobenzylamine salt of (1R)-1-[(N-benzyloxycarbonyl-sarcosyl-L-alanyl)amino]-ethylphosphonic acid of melting point 224°–226° C. (decomposition); $[\alpha]_D^{20} = -49.7°$; $[\alpha]_{365}^{20} = -182°$ (c=0.49% in water).

(ii) In a manner analogous to that described in Example 1(B)(ii), from the monobenzylamine salt of (1R)-1-[(N-benzyloxycarbonyl-sarcosyl-L-alanyl)amino]-ethylphosphonic acid there was obtained (1R)-1-(N-sarcosyl-L-alanylamino)-ethylphosphonic acid of melting point 245°–246° C. (decomposition); $[\alpha]_D^{20} = -84.2°$; $[\alpha]_{365}^{20} = -312°$ (c=0.5% in water).

EXAMPLE 28

(i) In a manner analogous to that described in Example 1(B)(i), from a solution of N-benzyloxycarbonyl-N-methyl-L-norvaline N-hydroxysuccinimide in dimethylformamide [prepared as described in Example 24(A)(iii)] and (1R)-1-(L-norvalylamino)-ethylphosphonic acid there was obtained the monobenzylamine salt of (1R)-1-[(N-benzyloxycarbonyl-N-methyl-L-norvalyl-L-norvalyl)amino]-ethylphosphonic acid of melting point 182°–184° C. (decomposition); $[\alpha]_D^{20} = -53.1°$; $[\alpha]_{365}^{20} = -198°$ (c=0.5% in acetic acid).

(ii) In a manner analogous to that described in Example 7(A)(ii) from the monobenzylamine salt of (1R)-1-[(N-benzyloxycarbonyl-N-methyl-L-norvalyl-L-norvalyl)amino]-ethylphosphonic acid there was obtained (1R)-1-(N-methyl-L-norvalyl-L-norvalylamino)-ethylphosphonic acid of melting point 294°–295° C. (decomposition); $[\alpha]_D^{20} = -52.6°$; $[\alpha]_{365}^{20} = -190°$ (c=0.5%, freshly prepared in 0.1-N sodium hydroxide).

EXAMPLE 29

(A) The Preparation of the Starting Material (i) In a manner analogous to that described in Example 15(B)(i), from (1R)-1-(L-norvalyl-L-norvalylamino)-ethylphosphonic acid [see Example 15(A)(ii)] and N-benzyloxycarbonyl-glycine N-hydroxysuccinimide ester there was obtained (1R)-1-[(N-benzyloxycarbonyl-glycyl-L-norvalyl-L-norvalyl)amino]-ethylphosphonic acid of melting point 195°–205° C. (decomposition).

(ii) In a manner analogous to that described in Example 5(A)(iii), from (1R)-1-[(N-benzyloxycarbonyl-glycyl-L-norvalyl-L-norvalyl)amino]-ethylphosphonic acid there was obtained (1R)-1-(glycyl-L-norvalyl-L-norvalylamino)-ethylphosphonic acid of melting point 268°–270° C. (decomposition); $[\alpha]_D^{20} = -83.1°$; $[\alpha]_{365}^{20} = -292°$ (c=0.4% in 1-N hydrochloric acid).

(B) The Process (i) In a manner analogous to that described in Example 15(B)(i), from (1R)-1-(glycyl-L-norvalyl-L-norvalylamino)-ethylphosphonic acid and a stock solution of N-benzyloxycarbonyl-sarcosine N-hydroxysuccinimide ester there was obtained (1R)-1-[(N-benzyloxycarbonyl-sarcosyl-glycyl-L-norvalyl-L-norvalyl)amino]-ethylphosphonic acid of melting point 210°–215° C. (decomposition).

(ii) In a manner analogous to that described in Example 5(A)(iii), from (1R)-1-[(N-benzyloxycarbonyl-sarcosyl-glycyl-L-norvalyl-L-norvalyl)amino]-ethylphosphonic acid there was obtained (1R)-1-(N-sarcosyl-glycyl-L-norvalyl-L-norvalylamino)-ethylphosphonic acid of melting point 278°–280° C. (decomposition); $[\alpha]_D^{20} = -85.8°$; $[\alpha]_{365}^{20} = -312°$ (c=0.51% in water).

EXAMPLE 30

(A) The Preparation of the Starting Material (i) In a manner analogous to that described in Example 15 (B)(i), from (1R)-1-(L-valyl-L-norvalylamino)-ethylphosphonic acid (prepared as described in Example 18) and N-benzyloxycarbonyl-L-valine N-hydroxysuccinimide ester [prepared as described in JACS, 86, 1839 (1964)], there was obtained (-R)-1-[(N-benzyloxycarbonyl-L-valyl-L-valyl-L-norvalyl)amino]-ethylphosphonic acid of melting point 257°–260° C. (decomposition).

(ii) In a manner analogous to that described in Example 5 (A)(iii), from (1R)-1-[(N-benzyloxycarbonyl-L-valyl-L-valyl-L-norvalyl)amino]-ethylphosphonic acid there was obtained (1R)-1-(L-valyl-L-valyl-L-norvalylamino)-ethylphosphonic acid of melting point ca 280° C. (decomposition); $[\alpha]_D^{20} = -70.9°$; $[\alpha]_{365}^{20} = -253°$ (c=0.48% in 1-N hydrochloric acid).

(B) The Process (i) In a manner analogous to that described in Example 15 (B)(i) from (1R)-1-(L-valyl-L-valyl-L-norvalylamino)-ethylphosphonic acid and a stock solution of N-benzyloxycarbonyl-sarcosine N-hydroxysuccinimide ester there was obtained 2.14 g of (1R)-1-[(N-benzyloxycarbonyl-sarcosyl-L-valyl-L-valyl-L-norvalyl)amino]-ethylphosphonic acid of melting point 257°–261° C. (decomposition).

(ii) In a manner analogous to that described in Example 5(A)(iii) from (1R)-1-[(N-benzyloxycarbonyl-sarcosyl-L-valyl-L-valyl-L-norvalyl)amino]-ethylphosphonic acid there was obtained (1R)-1-(N-sarcosyl-L-valyl-L-valyl-L-norvalylamino)-ethylphosphonic acid of melting point 292°–294° C. (decomposition); $[\alpha]_D^{20} = -87.9°$; $[\alpha]_{365}^{20} = -319°$ (c=0.33% in trifluoroacetic acid).

EXAMPLE 31

(A) The Preparation of the Starting Material (i)(a) In a manner analogous to that described in Example 1(B)(i), from N-benzyloxycarbonyl-L-norvaline N-hydroxysuccinimide ester and aminomethylphosphonic acid there was obtained the crude monobenzylamine salt of the desired product of melting point 195°–198° C. (decomposition). Recrystallization of a sample from hot water gave the pure monobenzylamine salt of (N-benzyloxycarbonyl-L-norvalyl)amino-methylphosphonic acid of melting point 203°–205° C. (decomposition); $[\alpha]_D^{20} = -8.2°$; $[\alpha]_{365}^{20} = -21.3°$ (c=0.5% in acetic acid).

(i)(b) 45.4 g (180 mmol) of N-benzyloxycarbonyl-L-norvaline were stirred in 200 ml of methylene chloride while 31.76 g (180 mmol) of dimethyl aminomethylphosphonate hydrochloride were added. The resulting suspension was cooled to −12° C. and 25.3 ml (180 mmol) of dry triethylamine were added dropwise. After completion of the addition, the cold mixture was stirred for 0.25 hour. 56.8 g (230 mmol) of 2-ethoxy-1-ethoxycarbonyl-1,2-dihydroquinoline in 100 ml of methylene chloride were then added rapidly. The mixture was stirred in the cold for 2 hours and then at room temperature overnight. The mixture was washed with 100 ml of water and then with four 100 ml portions of 1-N hydrochloric acid. The combined acid washings were back-extracted with two 50 ml portions of methylene chloride. The combined organic solutions were washed with 100 ml of water and finally with three 100 ml portions of 15% potassium bicarbonate solution, then dried over anhydrous sodium sulphate, filtered and evaporated. The residual oil was re-evaporated with benzene to give an oil which was triturated with 200 ml of anhydrous ether. There were obtained 58.2 g of crude product of melting point 77°–80° C. Recrystallization from 200 ml of ethyl acetate gave 50.6 g of dimethyl N-benzyloxycarbonyl-L-norvalyl-aminomethylphosphonate of melting point 82°–84° C.

(ii)(a) In a manner analogous to that described in Example 5(A)(iii) from the monobenzylamine salt of (N-benzyloxycarbonyl-L-norvalyl)amino-methylphosphonic acid there was obtained (L-norvalylamino)-methylphosphonic acid of melting point 273°–275° C. (decomposition); $[\alpha]_D^{20} = +61.2°$; $[\alpha]_{365}^{20} = +224°$ (c=0.54% in water).

(ii) (b) 37.2 g (100 mmol) of dimethyl N-benzyloxycarbonyl-L-norvalyl-aminomethylphosphonate were stirred for 5 hours in 120 ml of 45% hydrogen bromide in glacial acetic acid. 500 ml of diethyl ether were then added to precipitate an oil which was taken up in 300 ml of methanol. The solution was stirred and 40 ml of propylene oxide were added. After about 5 minutes, the product began to crystallise out and the mixture was left to stand in a refrigerator overnight. The solid was then filtered off and recrystallised from a mixture of 200 ml of hot water and 400 ml of ethanol to give 16.7 g of (L-norvalylamino)-methylphosphonic acid of melting point 293°–294° C. (decomposition); $[\alpha]_D^{20} = +62.7°$ (c=0.5% in water).

(iii) In a manner analogous to that described in Example 1(B) (i) from N-benzyloxycarbonyl-L-norvaline-N-hydroxysuccinimide ester and (L-norvalylamino)-methylphosphonic acid there was obtained, after triturating the residue from evaporation of the acid eluate with ether, ](N-benzyloxycarbonyl-L-norvalyl-L-norvalyl)amino]-methylphosphonic acid of melting point 175°–185° C. (decomposition).

(iv) In a manner analogous to that described in Example 5(A) (iii), from [(N-benzyloxycarbonyl-L-norvalyl-L-norvalyl)amino]-methylphosphonic acid there was obtained (L-norvalyl-L-norvalylamino)-methylphosphonic acid of melting point 265°–267° C. (decomposition); $[\alpha]_D^{20} = -12.4°$; $[\alpha]_{365}^{20} = -36.4°$ (c=0.51% in 1-N hydrochloric acid).

(B) The Process (i) In a manner analogous to that described in Example 1(B) (i), from (L-norvalyl-L-norvalylamino)-methylphosphonic acid and a stock solution of N-benzyloxycarbonyl-sarcosine N-hydroxysuccinimide ester there was obtained, after triturating the residue from evaporation of the acid eluate with ether, [(N-benzyloxycarbonyl-sarcosyl-L-norvalyl-L-norvalyl)amino]-methylphosphonic acid of melting point 205°–208° C. (decomposition).

(ii) In a manner analogous to that described in Example 5(A) (iii) from [(N-benzyloxycarbonyl-sarcosyl-L-norvalyl-L-norvalyl)amino]-methylphosphonic acid there was obtained (N-sarcosyl-L-norvalyl-L-norvalylamino)-methylphosphonic acid of melting point 271°–273° C. (decomposition); $[\alpha]_D^{20} = -56.2°$; $[\alpha]_{365}^{20} = -198°$ (c=0.55% in water).

EXAMPLE 32

(i) In a manner analogous to Example 1(B) (i), from a solution of N-benzyloxycarbonyl-N-methyl-L-valine N-hydroxysuccinimide ester in dimethylformamide and (1R)-1-(L-norvalyl-L-norvalylamino)-ethylphosphonic acid there was obtained the monobenzylamine salt of (1R)-1-[(N-benzyloxycarbonyl-N-methyl-L-valyl-L-norvalyl-L-norvalyl)amino]-ethylphosphonic acid of melting point 217°–227° C. (decomposition).

(ii) In a manner analogous to that described in Example 5(A) (iii), from the monobenzylamine salt of (1R)-1-[(N-benzyloxycarbonyl-N-methyl-L-valyl-L-norvalyl-L-norvalyl)amino]-ethylphosphonic acid there was obtained (1R)-1-(N-methyl-L-valyl-L-norvalyl-L-norvalylamino)-ethylphosphonic acid of melting point 300°–302° C. (decomposition).

EXAMPLE 33

(A) THE PREPARATION OF THE STARTING MATERIAL (i) In a manner analogous to that described in Example 31(A)(i)(b), from N-benzyloxycarbonyl-L-tyrosine and dimethyl (1R)-1-(L-alanylamino)ethylphosphonate there was obtained, after a final recrystallisation from methanol, the monomethanolate of dimethyl (1R)-1-[(N-benzyloxycarbonyl-L-tyrosyl-L-alanyl)amino]-ethylphosphonate of melting point 103°–106° C.

(ii) The monomethanolate of dimethyl (1R)-1-[(N-benzyloxycarbonyl-L-tyrosyl-L-alanyl)amino]-ethylphosphonate in methanol containing methanolic hydrochloric acid was hydrogenated in the presence of 10% palladium-on-charcoal. The catalyst was filtered off and the filtrate was evaporated. The residue was re-evaporated with toluene and suspended in ethanol/chloroform. The suspension was treated with N-benzyloxycarbonyl sarcosine and the resulting mixture was stirred at room temperature while triethylamine was added. After 0.25 hour, 2-ethoxy-1-ethoxycarbonyl-1,2-dihydroquinoline in chloroform was added. The mixture was stirred at room temperature overnight and evaporated, the residue was stirred with water, filtered off, washed and dried. After recrystallisation from methanol/diethyl ether, there was obtained dimethyl (1R)-1-[(N-benzyloxycarbonyl-sarcosyl-L-tyrosyl-L-alanyl)amino]-ethylphosphonate of melting point 119°–202° C.

(B) The Process (i) Dimethyl (1R)-1-[(N-benzyloxycarbonyl-sarcosyl-L-tyrosyl-L-alanyl)amino]-ethylphosphonate was stirred at room temperature for 18 hours in hydrochloric acid/acetic acid. The solution was evaporated and the residue was re-evaporated with toluene. The solid obtained was triturated with ether and dried. The solid was then taken up in methanol, aniline was added and the mixture was stirred for 1 hour. The aniline salt of (1R)-1-[(N-benzyloxycarbonyl-sarcosyl-L-tyrosyl-L-alanyl)amino]-ethylphosphonic acid was filtered off, washed with methanol and then with ether and finally dried: melting point 210°–214° C. (decomposition).

(ii) The aniline salt of (1R)-1-[(N-benzyloxycarbonyl-sarcosyl-L-tyrosyl-L-alanyl)amino]-ethylphosphonic acid was suspended in acetic acid and 10% palladium-on-carbon was added under argon. Acetic acid was then added. The mixture was stirred overnight at room temperature and then hydrogenated until the uptake of hydrogen ceased. The catalyst was filtered off and the filtrate was evaporated. The residual solid was triturated with methanol, filtered off, washed and dried. The solid was purified by reprecipitation from aqueous hydrochloric acid/ethanol with propylene oxide to give (1R)-1-(N-sarcosyl-L-tyrosyl-L-alanylamino)-ethylphosphonic acid of melting point 275°–277° C. (decomposition).

EXAMPLE 34

(A) THE PREPARATION OF THE STARTING MATERIAL (i) N-Benzylglycine hydrochloride was taken up in 2-N sodium hydroxide and the mixture was stirred at −5° C. while 4-N sodium hydroxide and benzyl chloroformate were simultaneously added dropwise. The mixture was stirred in the cold for 2 hours and then stirred at room temperature for 0.5 hour. Excess benzyl chloroformate was removed by extraction with ether. The aqueous layer was cooled to −5° C. and acidified with concentrated hydrochloric acid. The mixture was stirred in the cold for 1 hour, then brought to room temperature and extracted 4 times with diethyl ether. The diethyl ether extracts were back-washed with water, filtered and then dried over anhydrous sulphate and again filtered. Evaporation gave N-benzyl-N-benzyloxycarbonyl-glycine in the form of an oil.

(ii) In a manner analogous to that described in Example 31(A)(i)(b), from N-benzyloxycarbonyl-L-alanine and dimethyl (1R)-1-(L-alanylamino)-ethylphosphonate hydrochloride there was obtained dimethyl (1R)-1-[(N-benzyloxycarbonyl-L-alanyl-L-alanyl)amino]-ethylphosphonate of melting point 153°–155° C.

(iii) Dimethyl (1R)-1-[(N-benzyloxycarbonyl-L-alanyl-L-alanyl)amino]-ethylphosphonate was dissolved in methanol and catalytically hydrogenated in the presence of 10% palladium-on-charcoal. The solution was filtered and evaporated to give dimethyl (1R)-1-(L-alanyl-L-alanylamino)-ethylphosphonate in the form of an oil.

(B) THE PROCESS (i) Dimethyl (1R)-1-(L-alanyl-L-alanylamino)-ethylphosphonate was dissolved in methylene chloride and the solution was treated with N-benzyl-N-benzyloxycarbonyl-glycine. The resulting mixture was stirred, cooled to −10° C. and 2-ethoxy-1-ethoxycarbonyl-1,2- dihydroquinoline was added rapidly. The mixture was stirred in the cold for 2 hours and then at room temperature for 60 hours. After working-up in the usual manner, there was obtained dimethyl (1R)-[N-benzyl-benzyloxycarbonyl-glycyl-L-alanyl-L-alanyl)amino]-ethylphosphonate of melting point 114°–117° C.

(iii) In a manner analogous to that described in Example 5(A)(iii), from dimethyl (1R)-1-[(N-benzyl-N-benzyloxycarbonyl-glycyl-L-alanyl-L-alanyl)amino]-ethylphosphonate there was obtained (1R)-1-(N-benzyl-glycyl-L-alanyl-L-alanylamino)-ethylphosphonic acid of melting point 295°–296° C. (decomposition).

EXAMPLE 35

(A) THE PREPARATION OF THE STARTING MATERIAL (i) Ethyl bromoacetate in diethyl ether was added dropwise to a solution cooled to +5° C. of cyclopropylamine in diethyl ether. A white solid formed. The mixture was stirred for 3 hours while maintaining the cooling. The precipitate was filtered off and extracted with ether and the filtrate was evaporated. The residue was triturated with benzene/cyclohexane and the solid was filtered off. The filtrate was evaporated and the residue was distilled and fractionated to give ethyl cyclopropylaminoacetate of boiling point 32°–33° C./0.7 mmHg: $n_D^{19} = 1.4384$.

(ii) Ethyl cyclopropylaminoacetate was stirred in a mixture of concentrated hydrochloric acid and water until the reaction had subsided. The mixture was then heated to reflux for 2 hours. The resulting solution was evaporated to give a white solid which was triturated with acetone and recrystallised from methanol/ethyl acetate to give cyclopropylaminoacetic acid hydrochloride of melting point 189°–191° C. (decomposition).

(iii) In a manner analogous to that described in Example 34(A)(i), from cyclopropylaminoacetic acid hydrochloride and benzyl chloroformate there was obtained N-benzyloxycarbonyl-N-cyclopropyl-glycine in the form of an oil which eventually solidified. This was used in the next step without purification.

(B) The Process (i) In a manner analogous to that described in Example 31(A)(i)(b), from dimethyl (1R)-1-(L-alanyl-L-alanylamino)-ethylphosphonate [prepared as described in Example 34(A) (ii)] and benzyloxycarbonyl-N-cyclopropyl-glycine there was obtained dimethyl (1R)-1-[(N-benzyloxycarbonyl-N-cyclopropylglycyl-L-alanyl-L-alanyl)amino]-ethylphosphonate of melting point 120°–123° C.

(ii) In a manner analogous to that described in Example 5(A)(iii), from N-(1R)-1-[(N-benzyloxycarbonyl-N-cyclopropylglycyl-L-alanyl-L-alanyl)amino]-ethylphosphonate there was obtained (1R)-1-(N-cyclopropyl-glycyl-L-alanyl-L-alanylamino)-ethylphosphonic acid of melting point 287°–288° C. (decomposition).

EXAMPLE 36

(A) The preparation of the starting material

In a manner analogous to that described in Example 34(A)(i), from tert.butylaminoacetic acid hydrochloride and benzyl chloroformate there was obtained N-benzyloxycarbonyl-N-tert.butyl-glycine in the form of an oil.

(B) The Process (i) In a manner analogous to that described in Example 34(B)(i), from dimethyl (1R)-1-(L-alanyl-L-alanylamino)-ethylphosphonic acid and N-benzyloxycarbonyl-N-tert.butyl glycine there was obtained dimethyl (1R)-1-[(N-benzyloxycarbonyl-N-tert.butyl-glycyl-L-alanyl-L-alanyl)amino]-ethylphosphonate of melting point 75°–90° C.

(ii) In a manner analogous to that described in Example 34(A)(iii), from dimethyl (1R)-1-[(N-benzyloxycarbonyl-N-tert.butyl-glycyl-L-alanyl-L-alanyl)amino]-ethylphosphonate there was obtained dimethyl (1R)-1-[(N-tert.butyl glycyl-L-alanyl-L-alanyl)amino]-ethylphosphonate of melting point 148°–152° C.

(iii) In a manner analogous to that described in Example 5(A)(iii), from dimethyl (1R)-1-[(N-tert.butyl-glycyl-L-alanyl-L-alanyl)amino]-ethylphosphonate there was obtained (1R)-1-(N-tert.butyl-glycyl-L-alanyl-L-alanylamino)-ethylphosphonic acid of melting point 272°–274° C. (decomposition).

EXAMPLE 37

(i) In a manner analogous to that described in Example (34(B)(i), from dimethyl (1R)-1-(L-alanyl-L-alanylamino)-ethylphosphonate and N-benzyloxycarbonyl-N-henyl-glycine [prepared as described in J.Med.Chem., 15, (7), 720–726 (1972)] there was obtained dimethyl (1R)-1-[(N-benzyloxycarbonyl-N-phenyl-glycyl-L-alanyl-L-alanyl)amino]-ethylphosphonate of melting point 123°–125° C.

(ii) In a manner analogous to that described in Example 5(A)(iii), from dimethyl (1R)-1-[(N-benzyloxycarbonyl-N-phenyl-glycyl-L-alanyl-L-alanyl)amino]-ethylphosphonate there was obtained (1R)-1-(N-phenyl-glycyl-L-alanyl-L-alanylamino)-ethylphosphonic acid of melting point 216°–218° C. (decomposition).

EXAMPLE A

A 1000 ml injection solution containing the following ingredients was produced:

|  | Per 1000 ml |
|---|---|
| (1R)-1-(N-Sarcosyl-glycyl-L--alanylamino)-ethylphosphonic acid | 50.0 g |
| Chlorocresol | 1.0 g |
| Glacial acetic acid | 1.2 g |
| Sodium hydroxide solution (0.1-N) g.s. | ad pH 4.5 |
| Water for injection | ad 1000 ml |

We claim:

1. Compounds of the general formula

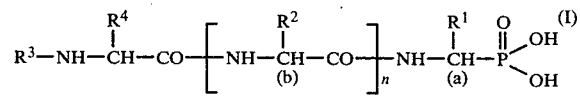

wherein $R^1$ represents a hydrogen atom or the methyl or hydroxymethyl group or a mono-, di- or trihalomethyl group; $R^2$ represents the characterising group of an α-amino acid of the type normally found in proteins or a lower alkyl or hydroxy-(lower alkyl) group other than the characterising group of an α-amino acid of the type normally found in proteins; $R^3$ represents a lower alkyl, lower cycloalkyl, or lower alkenyl; $R^4$ represents a hydrogen atom or a lower alkyl group; n stands for 1, 2 and 3; the configuration at the carbon atom designated as (a) is (R) when R¹ represents other than a hydrogen atom; and the configuration at the carbon atom designated as (b) is (L) when R² represents other than a hydrogen atom, and pharmaceutically acceptable salts thereof.

2. Peptide derivatives according to claim 1, wherein $R^1$ represents the methyl group.

3. Peptide derivatives according to claim 2, wherein both $R^2$'s represent the characterising group of an α-amino acid of the type normally found in proteins or a lower alkyl group other than the characterising group of an α-amino acid of the type normally found in proteins.

4. Peptide derivatives according to claim 3, wherein $R^3$ represents a lower alkyl group.

5. Peptide derivatives according to claim 4, wherein $R^3$ represents the methyl group.

6. The compound:
(1R)-1-(N-Sarcosyl-L-alanyl-L-alanylamino)-ethylphosphonic acid.

7. The compound:
(1R)-1-(N-Sarcosyl-L-alanyl-L-arginylamino)-ethylphosphonic acid.

8. The compound:
(1R)-1-(N-Methyl-L-norvalyl-L-norvalylamino)-ethylphosphonic acid.

9. The compound:
(1R)-1-(N-Methyl-L-norvalyl-L-norvalyl-L-norvalylamino)-ethylphosphonic acid.

10. The compound:
(1R)-1-(N-Sarcosyl-L-alanyl-L-norvalylamino)-ethylphosphonic acid.

11. The compound:
(1R)-1-(N-Sarcosyl-L-norvalyl-L-norvalylamino)-ethylphosphonic acid.

12. The compound:
(1R)-1-(N-Sarcosyl-L-norvalyl-L-arginylamino)-ethylphosphonic acid.

13. The compound:
(1R)-1-(N-Allyl-glycyl-L-alanyl-L-alanylamino)-ethylphosphonic acid.

14. Compounds of the general formula

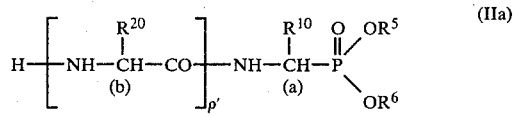

wherein e' stands for 2 or 3; $R^5$ and $R^6$ each represent a hydrogen atom or a lower alkyl group; $R^{10}$ represents a hydrogen atom or the methyl or hydroxymethyl group or a mono-, di or trihalomethyl group or a hydroxymethyl protected by a group selected from the group consisting of benzyloxycarbonyl, acetyl, propionyl, benzoyl, benzyl or tert-butyl; $R^{20}$ represents the characterising group of an α-amino acid of the type normally found in proteins or a lower alkyl or hydroxy-(lower alkyl) group other than such a characterising group, except that any amino group present may be protected by a group selected from the group consisting of benzyloxycarbonyl, tert-benzyloxycarbonyl, formyl, trityl, trifluoroacetyl and 2-(biphenylyl)-isopropyloxycarbonyl and with the proviso that at least one $R^{20}$ represents a lower alkyl or hydroxy-(lower alkyl) group other than said characterising groups or such a hydroxy-(lower alkyl) groups in which the hydroxy moiety is protected by a group selected from the group consisting of benzyloxycarbonyl, acetyl, propionyl, benzoyl, benzyl or tert-butyl; the configuration at the carbon atom (a) is (R) when $R^{10}$ is other than hydrogen; and the configuration at the carbon atom(s) (b) is (L) when $R^{20}$ is other than hydrogen.

15. Compounds of the general formula

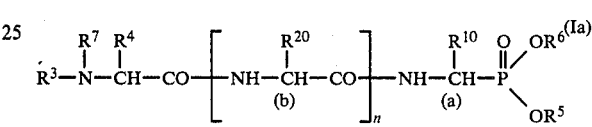

wherein $R^3$ represents a lower alkyl, lower cycloalkyl, or lower alkenyl; $R^4$ represents a hydrogen atom or a lower alkyl group; $R^5$ and $R^6$ each represent a hydrogen atom or a lower alkyl group; $R^7$ represents an amino protecting group selected from the group consisting of benzyloxycarbonyl, tert-benzyloxycarbonyl, formyl, trityl, trifluoroacetyl and 2-(biphenylyl)-isopropyloxycarbonyl; $R^{10}$ represents a hydrogen atom or the methyl or hydroxymethyl group or a mono-, di- or trihalomethyl group or a hydroxymethyl protected by a group selected from the group consisting of benzyloxycarbonyl, acetyl, propionyl, benzoyl, benzyl or tert-butyl; $R^{20}$ represents the characterising group of an α-amino acid of the type normally found in proteins or a lower alkyl or hydroxy-(lower alkyl) group other than such a characterising group, except that any amino group present may be protected by a group selected from the group consisting of benzyloxycarbonyl, acetyl, propionyl, benzoyl, benzyl or tert-butyl; n stands for 1, 2 or 3; the configuration at the carbon atom (a) is (R) when $R^{10}$ is other than hydrogen; and the configuration at the carbon atom(s) (b) is (L) when $R^{20}$ is other than hydrogen.

* * * * *